(12) United States Patent
Filee et al.

(10) Patent No.: US 8,545,853 B2
(45) Date of Patent: Oct. 1, 2013

(54) **RECOMBINANT ALPHA-HEMOLYSIN POLYPEPTIDE OF *STAPHYLOCOCCUS AUREUS*, HAVING A DELETION IN THE STEM DOMAIN AND HETEROLOGOUS SEQUENCES INSERTED**

(75) Inventors: Patrice Filee, Liege (BE); Noureddine Rhazi, Liege (BE); Moreno Galleni, Liege (BE); Bernard Taminiau, Liege (BE); Olivier Jolois, Liege (BE); Alfred Collard, Marloie (BE); Alain Jacquet, Brussels (BE)

(73) Assignees: Universite de Liege, Angleur (BE); Centre d'Economie Rurale, Marloie (BE); Universite Libre de Bruxelles, Bruxelles (BE)

( * ) Notice: Subject to any disclaimer, the term of this patent is extended or adjusted under 35 U.S.C. 154(b) by 0 days.

(21) Appl. No.: 13/143,795

(22) PCT Filed: Jan. 15, 2010

(86) PCT No.: PCT/EP2010/050453
§ 371 (c)(1),
(2), (4) Date: Sep. 27, 2011

(87) PCT Pub. No.: WO2010/081875
PCT Pub. Date: Jul. 22, 2010

(65) Prior Publication Data
US 2012/0014983 A1   Jan. 19, 2012

(30) Foreign Application Priority Data
Jan. 19, 2009 (EP) .................................... 09150888

(51) Int. Cl.
*A61K 39/09* (2006.01)
*A61K 39/02* (2006.01)
*A61K 39/00* (2006.01)
*A61K 39/085* (2006.01)
*A61K 38/00* (2006.01)
*C07K 1/00* (2006.01)

(52) U.S. Cl.
USPC ............. 424/237.1; 424/236.1; 424/234.1; 424/190.1; 424/184.1; 424/243.1; 530/350; 530/806; 530/825; 514/1.1

(58) Field of Classification Search
None
See application file for complete search history.

(56) References Cited

U.S. PATENT DOCUMENTS

2004/0191845 A1* 9/2004 Bayley et al. ................ 435/7.33
2010/0047267 A1* 2/2010 Masignani et al. ........ 424/190.1

FOREIGN PATENT DOCUMENTS

| WO | 9905167 A | 2/1999 |
| WO | 2007145689 A | 12/2007 |

OTHER PUBLICATIONS

Greenspan et al. Nature Biotechnology 17:936-937, 1999.*
Skolnick et al. Trends in Biotechnology 18: 34-39, 2000.*
Werner, et al., "Retrieving Biological Activity from LukF-PV Mutants Combined with Different S Components Implies Compatibility between the Stem Domains of These Staphylococcal Bicomponent Leucotoxins", Infection and Immunity, vol. 70, No. 3, Mar. 2002, p. 1310-1318.
International Search Report and Written Opinion, issued on May 3, 2010 for International Application No. PCT/EP2010/050453.

* cited by examiner

*Primary Examiner* — S. Devi
(74) *Attorney, Agent, or Firm* — Knobbe, Martens, Olson & Bear LLP

(57) ABSTRACT

It refers to a recombinant alpha-hemolysin polypeptide of *Staphylococcus aureus*, comprising a deletion in the stem domain, wherein at least one heterologous sequence is inserted in a region selected from the group consisting of regions defined by amino acid position of 108 to 151, 1 to 5, 288 to 293, 43 to 48, 235 to 240, 92 to 97, 31 to 36,or 156 to 161 of SEQ ID NO: 1, with the proviso that, if the heterologous sequence contains five or more consecutive histidines the moiety of the heterologous sequence other than the moiety of five or more consecutive histidines has a minimum length of 11 amino acids; or a variant thereof comprising 1-50 amino acids added, substituted or deleted in SEQ ID NO. 1 and the activity to form oligomers and to bind to lipidic bilayers. It also provides a medicament and vaccine comprising said recombinant polypeptide.

16 Claims, 19 Drawing Sheets

A.

B.

A

B

RECOMBINANT ALPHA-HEMOLYSIN POLYPEPTIDE OF *STAPHYLOCOCCUS AUREUS*, HAVING A DELETION IN THE STEM DOMAIN AND HETEROLOGOUS SEQUENCES INSERTED

RELATED APPLICATIONS

This application is a U.S. National Phase of International Application No. PCT/EP2010/050453, filed Jan. 15, 2010, designating the U.S., and published in French as WO 2010/081875 on Jul. 22, 2010 which claims the benefit of European Patent Application No. 09150888.7 filed Jan. 19, 2009.

FIELD OF THE INVENTION

The invention is related to the development of an engineered form of bacterial alpha-hemolysin. In particular, the present invention refers to a recombinant single-chain alpha-hemolysin polypeptide of *Staphylococcus aureus,* which has a deletion in the stem domain and comprises at least one additional heterologous sequence inserted into permissive sites of said recombinant alpha-hemolysin polypeptide.

BACKGROUND OF THE INVENTION

Since the development of recombinant DNA techniques in the late 1970s, gene fusion technology has been used for generating multifunctional proteins for a broad range of applications. Fusion proteins are utilised in protein science research for diverse applications. In order to construct such fusion proteins, two types of connection are possible. One is 'end to end' fusion in which the N-terminus of one domain is linked to the C-terminus of the other domain. The second is "insertional" fusion in which one domain is inserted in-frame into the middle of the other parent domain.

Proteins or fragments thereof are used for active immunization. Active immunization involves trying to stimulate humoral and cellular immune responses by administering antigens. These antigens can be killed or weakened forms of the disease-causing agents, subunits of the infectious agents and recombinant proteins corresponding to the native proteins or to polyepitopes. Passive immunization involves giving antibodies called gamma globulins to someone who was infected with the disease.

A major obstacle in vaccine development is variability, complexity and adaptability of pathogens. For instances, the variability of *S. aureus* is associated with its twelve serotypes which are related to the capsular polysaccharide composition. The complexity of this microorganism is due to its phenotype because *S. aureus* is able to produce more that forty virulence factors. The adaptability is related to the capacity of the bacteria to accumulate mutations and to become resistant to antibiotic treatment or even more to escape to the immune system. This explains the tendency of some pharmaceutical groups to develop multivalent vaccine by combining several antigens in a same vaccine formulation. In this context, a vaccine consisting of a single protein would be less costly to manufacture and has the advantage of a practical production process and more straightforward quality control testing than a vaccine consisting of several recombinant proteins.

Epitope characterization is medically important in application such as vaccination and antibodies developments. There are a number of advantages to immunize only with the epitope rather than with the entire organism or with the isolated antigen such as the safety, the difficulties to obtain pure antigens, the problems of immunodominance of some epitopes or the possibility to focus the immune response on protein regions which are of crucial importance for the biological activity of the protein.

If various epitope mapping techniques have permitted to unravel antibody/antigen interactions, the possibilities to deliver these small B cell epitopes to the immune system are lacking. According to the literature, the classical approaches that consist simply to fuse epitopes gives rise to polypeptides that are poorly antigenic. An alternative approach of epitope-vaccines is the conjugation to a carrier able to elicit an efficient T cell help for antibody producing B cells. Consequently, this is this feature that limits drastically the use of epitope-vaccines obtained by gene fusion. In this way, virus-like particles have demonstrated to be suitable molecular scaffold of B cell epitopes. But this approach is often confronted to the "assembly problem" occurring when the epitope fusion or insertion prevent assembling of the core protein to form the virus-like particle.

*Staphylococcal* alpha-hemolysin (HA) is secreted by most strains of *Staphylococcus aureus* as a water soluble monomer of 293 residue polypeptide. This toxin forms heptameric pores in membranes of susceptible cells such as platelets, erythrocytes, peripheral blood monocytes, macrophages, keratinocytes, fibroblasts and endothelial cells. HA is endowed with haemolytic, cytotoxic, demonecrotic and lethal properties as well in humans as in animals. A role of this toxin in *Staphylococcus aureus* biofilm formation and more precisely in cell-to-cell interactions was also reported. The crystal structure of the heptamer HA in detergent indicates a mushroom-shaped object in which the lower half of the stem (K110 to Y148), a 14 strand β-barrel, forms a transmembrane channel made up of residues from the seven central-glycine-rich regions of the polypeptide chains (FIG. 1). The N- and C-terminal third of the polypeptide is organized in a β-sandwich structure that participates to the formation of the cap of the mushroom located outside of the targeted cell.

*Staphylococcus aureus* is a hardy, Gram-positive bacterium that is frequent cause of both community-acquired and nosocomial disease. Transient asymptomic colonization is common, occurring in up to 40% of children and adults.

In a minority of cases, *S. aureus* infection is associated with severe disease, including bacteremia, osteomyelitis, endocarditis, meningitis and abscess formation. *S. aureus* infections are relatively difficult to treat, and invasive diseases and relapse may occur following antibiotic treatment.

The infections caused by *S. aureus* are also problematic in animals. Bovine mastitis is the most costly disease to the dairy industry worldwide, with losses estimated at 2 billion dollars per year in the United States alone. Mastitis is the primary reason for culling, e.g. mastitis was reported to be the reason for 15% of the cows culled in the USA. *S. aureus* is one of the most frequent causes of bovine mastitis, and despite several decades of research aimed at controlling this pathogen, it remains a substantial economic problem to milk producers worldwide.

Treatment is made more difficult by the increasing number of strains that are resistant to multiple antibiotics, including methicillin. Resistance to vancomycin, an antibiotic of last resort, has also developed recently. Disease prevention is therefore the best way to limit the morbidity and mortality caused by this organism as well in humans as animals. As whole-cell live or killed vaccines largely fail to generate protective immune responses, alternative immunizations have been tested such as:

Active Immunizations:

Capsular polysaccharides act as virulence factors by reducing the ability of host polymorphonuclear neutrophils to opsonise the bacteria. Although 12 *S. aureus* capsular polysaccharides have been identified, types 5 and 8 have historically accounted for the majority of *S. aureus* diseases. A vaccine has been developed that contains type 5 and 8 polysaccharides (StaphVAX®, Nabi Biopharmaceuticals). Its protective capacity has been demonstrated in a mouse model. It has also been shown to be safe and immunogenic in humans. Although it is the only staphylococcal vaccine to date that has been tested in a Phase III clinical trial, it failed to meet the goals of this Phase III clinical trials.

Immunization with poly-N-acetylglucosamine, a *S. aureus* surface carbohydrate synthesized by icaABC products, has been shown to protect mice against *staphylococcal* disease.

Subunit vaccines composed of individual surface proteins, for example, clumping factor A (ClfA), clumping factor B (ClfB), iron-regulated surface determinant B (IsdB), or fibronectin-binding protein (FnBP), generate immune responses that afford partial protection against *S. aureus* challenge of experimental animals.

Passive Immunizations:

Monoclonal antibodies were currently being tested for their ability to interfere with *staphylococcal* infections. A formulation containing high levels of opsonising antibodies against *S. aureus* capsular polysaccharide types 5 and 8 (Altastaph™, Nabi Biopharmaceuticals) is currently in clinical trials.

Teichoic acid is a polymer expressed on the surface of *S. aureus* that is present in two forms: wallteichoic acid (WTA), a major component of *staphylococcal* cell wall, and lipoteichoic acid (LTA), which is connected to the cell membrane. A monoclonal anti-LTA antibody is currently being tested for its ability to prevent coagulase-negative *staphylococcal* sepsis. A phase I/II double-blind, placebo-controlled study of the anti-LTA monoclonal antibody demonstrated that the antibody is safe and tolerable in premature infants and shows linear pharmacokinetics. Efficacy trials have not been reported.

Veronate, a passive immunotherapy developed by Inhibitex, based on the humanized monoclonal antibodies recognizing the *S. aureus* ClfA protein and *S. epidermidis* SdrG. These monoclonal antibodies show some protective efficacy in animal models of *S. aureus* infection.

The document WO2007/145689 A1 refers to vaccines comprising an *S. aureus* alpha-toxin and a pharmaceutically acceptable carrier, wherein the *S. aureus* alpha-toxin antigen may contain at least two alterations that reduce its toxicity and/or may be conjugated to or co-administrated with another bacterial antigen. The vaccines may comprise one or more other bacterial antigens. According to WO2007/145689 alpha-hemolysin protein alone is used as antigen and/or is chemically conjugated with other *S. aureus* antigens. However, the disadvantage of conjugated proteins is that cross-linking will compromise structure, activity, immunogenicity and antigenicity. Further, each protein component to be mixed together or to be conjugated has a different purification history due to different physico-chemical properties, has a different degree of purity, and possibly has different impurities In addition, it is difficult to control the stoechiometry of the chemical conjugation between the different proteins leading to a problem of heterogeneity in the protein solution. Therefore, maintaining the same quality of different charges is difficult. In addition, conjugation of proteins result in a mixture of different products which can not properly defined.

SUMMARY OF THE INVENTION

The object of the present invention was to develop a versatile tool which permits:

(i) to overproduce polypeptides difficult to express;

(ii) to display simultaneously one to several heterologous polypeptides in a unique protein;

(iii) to design new multivalent antigens that could be used in vaccinal preparations, particularly for the preventive and/or therapeutic treatment of diseases caused by *Staphylococcus*;

(iv) to design new multivalent antigens that could be used in as antigenic sources for antibody developments;

(v) to elicit antibody production against heterologous polypeptides corresponding to native epitopes and/or mimotopes.

(vi) to provide a system for an oriented immobilisation of proteins at the surface of liposomes or any types of lipidic layers, for studying protein interactions by using diverse techniques such as ELISA, Biacore, Biosensor.

(vii) to provide a defined protein e.g. for use as medicament or vaccine, which can be prepared in essentially the same purity and quality.

The object of the present invention is solved by a recombinant single-chain alpha-hemolysin polypeptide of Staphylococcus aureus, having a deletion in the stem domain for removing hemolytic activity, wherein at least one heterologous sequence is inserted in a region selected from the group consisting of regions defined by amino acid position 108 to 151 (site 1), amino acid position 1 to 5 (site 2), amino acid position 288 to 293 (site 3), amino acid position 43 to 48 (site 4), amino acid position 235 to 240 (site 5), amino acid position 92 to 97 (site 6), amino acid position 31 to 36 (site 7), amino acid position 156 to 161 (site 8) in respect to the wild-type sequence SEQ ID NO: 1, with the proviso that, if the heterologous sequence contains five or more consecutive histidine residues the moiety of the heterologous sequence other than the moiety represented by said five or more consecutive histidine residues has a minimum length of 11 amino acid residues.

The present invention is also solved by a variant of said recombinant single-chain alpha-hemolysin polypeptide, wherein in addition to said deletion in the stem domain and said insertion of heterologous sequence, 1 to 50 amino acid residues are added, substituted or deleted in respect to the wild-type sequence SEQ ID NO: 1 and has the activity to form oligomers and to bind to lipidic bilayers, including lipidic mono layers and lipidic bilayers, or cell membranes.

The deletion in the stem domain or the insertion of heterologous sequences into the mentioned insertion sites do not abolish the activity to form oligomers or to bind to lipidic layers, including lipidic mono layers and lipidic bilayers, or cell membranes.

If the heterologous sequence contains five or more consecutive histidine residues the moiety of the heterologous sequence other than the moiety represented by said five or more consecutive histidine residues has a minimum length of preferably 15, further preferred 20, more preferred 25 amino acid residues.

In further preferred embodiments a variant of said recombinant single-chain alpha-hemolysin polypeptide preferably is provided, wherein 1 to 40 amino acid residues, preferred 1 to 25 amino acid residues, further preferred 1 to 20 amino acid residues, further preferred 1 to 15 amino acid residues, still further preferred 1 to 10 amino acid residues, most preferred 1 to 5 amino acid residues are added, substituted or deleted in respect to the wild-type sequence SEQ ID NO:

1, in addition to said deletion in the stem domain and said insertion of heterologous sequence and has the activity to form oligomers and to bind to lipidic layers, including lipidic mono layers and lipidic bilayers, or cell membranes.

A further preferred embodiment of the present invention is that the alpha-hemolysin polypeptide comprises at least one heterologous sequence inserted in a region selected from the group consisting of regions defined by amino acid position 108 to 151 (site 1), amino acid position 43 to 48 (site 4), amino acid position 235 to 240 (site 5), amino acid position 92 to 97 (site 6), amino acid position 31 to 36 (site 7), amino acid position 156 to 161 (site 8) in respect to the wild-type sequence SEQ ID NO: 1. In addition to said insertion the recombinant alpha-hemolysin polypeptide may have at least one further heterologous sequence inserted in a region defined by amino acid position 1 to 5 (site 2) and/or amino acid position 288 to 293 (site 3) in respect to the wild-type sequence SEQ ID NO: 1.

In an even further preferred embodiment the alpha-hemolysin polypeptide comprises at least one heterologous sequence inserted in a region defined by amino acid position 108 to 151 (site 1) in respect to the wild-type sequence SEQ ID NO: 1. In addition to said insertion the recombinant alpha-hemolysin polypeptide may have at least one further heterologous sequence inserted in a region selected from the group consisting of regions defined by amino acid position 1 to 5 (site 2), amino acid position 288 to 293 (site 3), amino acid position 43 to 48 (site 4), amino acid position 235 to 240 (site 5), amino acid position 92 to 97 (site 6), amino acid position 31 to 36 (site 7), amino acid position 156 to 161 (site 8) in respect to the wild-type sequence SEQ ID NO: 1.

As mentioned above, the recombinant alpha-hemolysin polypeptide according to the invention has a deletion in the stem domain: this deletion in the stem domain serves the purpose to abolish toxicity of the alpha-hemolysin and is achieved by that the polypeptide does not anymore form a pore in the cell membrane. The stem domain lies within the amino acid sequence from Thr109 to Gln150 in respect to the wild-type sequence SEQ ID NO: 1. In a preferred embodiment the amino acid sequence from Thr109 to Gln150 in respect to the wild-type sequence SEQ ID NO: 1 is partially or completely removed. Further preferred, the amino acid sequence from Thr109 to Gln150 in respect to the wild-type sequence SEQ ID NO: 1 is completely removed.

Further preferred, the region (Thr109 to Gln150) which includes the stem region (K110 to Y148) and some amino acids of the triangle region, has been substituted with the tripeptide PGN (see table 1). The nucleotide sequence of the tripeptide is used to create an insertion site of heterologous polypeptides in the nucleotidic sequence of the alpha hemolysin encoding gene. As a result, the protein loses its hemolytic activity. The region Thr109 to Gln150 of alpha-hemolysin is very suitable for insertion and display of large polypeptides. This is because the substitution of this region does not damage the other biological activities of the protein (correct folding, binding to lipidic layer, oligomer formation). In regard to the 3D structure, the present inventors found that the stem domain and thus the insertion site are flanked with a natural linker which corresponds to the triangle region. This region spaces the core of the protein to the stem domain so that they have a folding which is independent to the other. This explains why insertion of polypeptides having a higher size than the stem domain is still permissive (for instance see results with PBP2a [SEQ ID NO: 10] and ClfA [SEQ ID NO: 14]). No previous data describes this feature.

In a preferred embodiment of the present invention the heterologous sequence has a minimum length of 5 amino acid residues, preferably at least 8, at least 10, at least 12, at least 15, at least 20, at least 30, at least 50, at least 75, at least 100, at least 150, at least 200, at least 300 amino acid residues.

In a further preferred embodiment of the present invention the heterologous sequence has a maximum length of 3000 amino acid residues, preferably a maximum length of 2000, further preferred a maximum length of 1500, even further preferred a maximum length of 1000, still further preferred a maximum length of 500, further preferred a maximum length of 250 and most preferred a maximum length of 100 amino acid residues.

According to a further preferred embodiment of the present invention the recombinant alpha-hemolysin polypeptide comprises at least two heterologous sequences inserted in the same of said insertion sites or inserted in different of said insertion sites. This means that each of two or more heterologous sequences are inserted separately into the provided insertion sites. As alternative two or more heterologous sequences may also be arranged consecutively and inserted into the provided insertion sites. The two or more heterologous sequences inserted into the same or different insertion sites may be the same sequence or different. Preferably, each of two or more heterologous sequences different from each other are inserted separately into the provided insertion sites. As alternative two or more heterologous sequences different from each other may also be arranged consecutively and inserted into the provided insertion sites.

As used herein the term "heterologous sequence" refers to any amino acid sequence other than alpha-hemolysin sequence. The "heterologous sequence" or "heterologous sequences" may be of any origin including virus, bacteria, plant, fungi, parasites, animal or human or even an arbitrary artificial sequence. The heterologous sequence could correspond to B-cell or T-cell epitopes. It also includes mimotopes, peptide which mimics the structure of an epitope. Because of this property it causes an antibody response identical to the one elicited by the native epitope. In this case, the native epitope could also correspond to macromolecules which are not related to protein such as peptidoglycan, teichoic acid, capsular polysaccharide.

In a particularly preferred embodiment the heterologous sequence or heterologous sequences is/are exclusively derived from *Staphylococcus* species, preferably *Staphylococcus aureus*.

The *S. aureus* genome is composed of core and auxiliary genes which encode secreted proteins, peptidoglycan and membrane-anchored proteins and cytoplasmic proteins. The majority of genes comprising the core genome are those associated with central metabolism and other housekeeping functions of the vegetative life of the bacteria, such as DNA replication, protein synthesis, and carbohydrate metabolism. Supplementing these are auxiliary genes that are not essential for growth and survival, including virulence genes. The majority of virulence genes are:

(i) Surface binding proteins, several of these related proteins bind extracellular-matrix molecules and have been designated MSCRAMM for microbial-surface components recognizing adhesive matrix molecules (e.g. clumping factors, fibronectin-binding proteins, collagen-binding proteins, and bore sialoprotein-binding proteins).
(ii) Virulence factors involved in evading and/or destroying host defenses such Leukocidins (e.g., PVL and γ-toxin), capsular polysaccharides (e.g., 5 and 8), protein A, Extracellular adherence protein (Eap).
(iii) Virulence factors involved in tissue invasion and/or penetration such proteases, lipases, nucleases, hyaluronate lyase, phospholipase C, and metalloproteases.
(iv) Virulence factors involved in toxin-mediated disease and/or sepsis such Enterotoxins, toxic shock syndrome toxin-1, exfoliative toxins A and B, α-toxin.
(v) Virulence factors involved in persistence such biofilm accumulation, small-colony variants.

(vi) Virulence factors involved in antibiotic resistance mechanism such β-lactamase, PBP2a a resistant penicillin-binding protein.
(vii) Mimotopes corresponding to a variety of *Staphylococcal* antigens, including peptidoglycan, teichoic acid, lipoteichoic acid and capsular polysaccharides.

A mimotope is a macromolecule, often a peptide, which mimics the structure of an antigen epitope, When applied for immunizations they induce desired antibody specificities exclusively based on the principle of molecular mimicry. The concept of mimotope not only provides a clue for analyzing antigen epitope, but also presents a new way for development of vaccine. Mimotope usually represents a polypeptide structure that can mimic an antigen epitope and has a reactionogenicity similar to that of native antigen. When the mimotope is conjugated to a suitable carrier, it may exhibit similar immunogenicity (the native antigen may not comprise an identical or similar sequence or spatial structure). The studies of some antigens that are difficult to be obtained or identified can hardly be conducted, because their antigen epitopes can hardly determined, but this problem may be solved by obtaining their mimotopes. Mimotope provides a clue for analyzing antigen epitope and gives a new way for development of vaccine; moreover, it promotes the researches of conformational epitopes and non-protein antigen epitopes.

Further preferred, the heterologous sequence or heterologous sequences is/are selected from the group consisting of SEB (*Staphylococcus aureus* enterotoxin B), TSST (toxic shock syndrome toxine), FnBP (fibronectin-binding protein), BlaZ (β-lactamase), ClfA (Clumping Factor A), PBP2a (penicillin-binding protein 2a), Protein A, all derived from Staphylococcus species, preferably *Staphylococcus aureus*.

In yet another particularly preferred embodiment the heterologous sequence or heterologous sequences is/are selected from sequences SEQ ID NOs: 7 to 18 (see table 2).

In addition, the present invention provides the recombinant alpha-hemolysin polypeptides according to table 3.

In a further particularly preferred embodiment the heterologous sequence comprises a fragment of the immunoglobulin G-binding domain of protein A of *Staphylococcus* species, preferably of *Staphylococcus aureus;* wherein said fragment of the immunoglobulin G-binding domain of protein A is having a minimum size of 5 amino acid residues and has no or reduced binding activity to Fc or Fab domain of immunoglobulin G compared to full-length protein A. In a preferred embodiment of the present invention the fragment of the immunoglobulin G-binding domain of protein A is having a minimum length of 5 amino acid residues, preferably at least 8, at least 10, at least 12, at least 15, at least 20, at least 25, at least 30 amino acid residues.

In a further preferred embodiment of the invention the fragment of the immunoglobulin G-binding domain of protein A is having a length of 5 to 35 amino acid residues, preferably 5 to 30 amino acid residues, further preferred 10 to 30 amino acid residues, and even further preferred 10 to 25 amino acid residues.

Further preferred, the fragment of the immunoglobulin G-binding domain of protein A covers not more than two complete alpha-helices.

In a further preferred embodiment of the present invention said fragment of the immunoglobulin G-binding domain of protein A has no or reduced binding activity to Fc and has no or reduced binding activity to Fab domain of immunoglobulin G compared to full-length protein A. In a particularly preferred embodiment of the present invention said fragment of the immunoglobulin G-binding domain of protein A has no significant binding activity to Fc and has no significant binding activity to Fab domain of immunoglobulin G.

The selection of a certain limited size of the fragment of the immunoglobulin G-binding domain of protein A makes sure that the fragment does not have a significant Fab or Fc binding activity. As mentioned above, the binding activity of protein A immunoglobulin G binding domains requires the presence of the three alpha-helices (helix 1, helix 2 and helix 3). For the purpose to develop a vaccine against Staphylococcus the fragment of the immunoglobulin G-binding domain of protein A shall have no significant Fab or Fc binding activity. The person skilled in the art will be able to chose fragments of protein A immunoglobulin G binding domains for insertion into the detoxified HA molecule so that said fragment will have no significant Fab or Fc binding activity, e.g. by choosing a fragment covering not more than one or two complete helices of the three-helical bundle fold (helix 1, helix 2 and helix 3).

In a further preferred embodiment the fragment of protein A immunoglobulin G binding domains comprises the sequence of not more than one complete helix selected from helix 1, helix 2 and helix 3 of the immunoglobulin G (IgG)-binding domains E, D, A, B, and C.

In yet another particularly preferred embodiment the fragment of protein A is selected from sequences SEQ ID NOs: 16 to 18 (see table 2).

According to a preferred embodiment the alpha-hemolysin moiety of the recombinant polypeptide of the present invention is having the sequence SEQ ID NO: 3 or SEQ ID NO: 5 (ICHA I, ICHA II). In addition, variants of the said recombinant single-chain alpha-hemolysin polypeptide are comprised wherein the alpha-hemolysin moiety has 80% or more, preferably 85% or more, further preferred 90%, most preferred 95% or more amino acid identity in respect to the sequences SEQ ID NO: 3 or SEQ ID NO: 5.

The present invention also provides a polynucleotide encoding the above described recombinant alpha-hemolysin polypeptide according to the present invention. Further provided is a vector comprising said polynucleotide encoding the above described recombinant alpha-hemolysin polypeptide. Also provided is a transformant comprising the polynucleotide encoding the above described recombinant alpha-hemolysin polypeptide or the vector comprising said polynucleotide encoding the above described recombinant alpha-hemolysin polypeptide.

The recombinant polypeptide can be used in prevention and/or therapy, particularly of diseases caused by *Staphylococcus* spec. particularly of *Staphylococcus aureus*. The polynucleotide or the vector as mentioned above can be used in DNA vaccination.

The object is also solved by a medicament or vaccine comprising a recombinant single-chain alpha-hemolysin polypeptide of *Staphylococcus aureus,* having a deletion in the stem domain for removing hemolytic activity, wherein at least one heterologous sequence is inserted in a solvent-exposed loop of alpha-hemolysin polypeptide, wherein the heterologous sequence or heterologous sequences is/are selected from *Staphylococcus* species, preferably *Staphylococcus aureus*. The heterologous sequence or heterologous sequences is/are selected from the house keeping proteins, virulence factors (cytoplasmic, secreted, and anchored proteins to the cytoplasmic membrane or peptodoglycan) and mimotopes corresponding to a variety of *Staphylococcal* antigens, including peptidoglycan, teichoic acid, lipoteichoic acid and capsular polysaccharides.

As used herein the term "solvent-exposed loop" means that the respective part of the amino acid sequence of alpha-hemolysin polypeptide, which is forming a loop, is exposed to and accessible from an aqueous medium or biological fluids such a blood.

In a preferred embodiment of the medicament or vaccine the heterologous sequence or heterologous sequences is/are selected from the group consisting of SEB (*Staphylococcus aureus* enterotoxin B), TSST (toxic shock syndrome toxine), FnBP (fibronectin-binding protein), BlaZ (β-lactamase), ClfA (Clumping Factor A), PBP2a (penicillin-binding protein 2a), Protein A, all derived from *Staphylococcus* species, preferably *Staphylococcus aureus*.

In a preferred embodiment of the medicament or vaccine the heterologous sequence is inserted in a region selected from the group consisting of regions defined by amino acid position 108 to 151 (site 1), amino acid position 1 to 5 (site 2), amino acid position 288 to 293 (site 3), amino acid position 43 to 48 (site 4), amino acid position 235 to 240 (site 5), amino acid position 92 to 97 (site 6), amino acid position 31 to 36 (site 7), amino acid position 156 to 161 (site 8), preferably into a region defined by amino acid position 108 to 151, in respect to the wild-type sequence SEQ ID NO: 1.

In yet another particularly preferred embodiment of the medicament or vaccine the heterologous sequence or heterologous sequences is/are selected from sequences SEQ ID NOs: 7 to 18 (see table 2). It is preferred that at least 2, preferably at least 3, further preferred at least 4 different heterologous sequences are selected from sequences SEQ ID NOs: 7 to 18.

In addition, in a further particularly preferred embodiment the medicament or vaccine comprises a recombinant alpha-hemolysin polypeptide selected from the group as shown in table 3.

As mentioned above, the recombinant alpha-hemolysin polypeptide according to the invention comprised in the medicament or vaccine has a deletion in the stem domain, namely within the amino acid sequence from Thr109 to Gln150 in respect to the wild-type sequence SEQ ID NO: 1. In a preferred embodiment the amino acid sequence from Thr109 to Gln150 in respect to the wild-type sequence SEQ ID NO: 1 is partially or completely removed. Further preferred, the amino acid sequence from Thr109 to Gln150 in respect to the wild-type sequence SEQ ID NO: 1 is completely removed.

According to a preferred embodiment of the medicament or vaccine the alpha-hemolysin moiety of the recombinant polypeptide of the present invention is having the sequence SEQ ID NO: 3 or SEQ ID NO: 5 (ICHA I, ICHA II). In addition, variants of the said recombinant single-chain alpha-hemolysin polypeptide are comprised wherein the alpha-hemolysin moiety has 80% or more, preferably 85% or more, further preferred 90%, most preferred 95% or more amino acid identity in respect to the sequences SEQ ID NO: 3 or SEQ ID NO: 5.

A preferred embodiment of the medicament or vaccine has the proviso that, if the heterologous sequence contains five or more consecutive histidine residues the moiety of the heterologous sequence other than the moiety represented by said five or more consecutive histidine residues has a minimum length of 11 amino acid residues.

If the heterologous sequence contains five or more consecutive histidine residues the moiety of the heterologous sequence other than the moiety represented by said five or more consecutive histidine residues has a minimum length of preferably 15, further preferred 20, more preferred 25 amino acid residues.

The recombinant single-chain alpha-hemolysin polypeptide comprised in the medicament or vaccine according to the invention may comprise any one or more of the features described above for the recombinant single-chain alpha-hemolysin polypeptide.

The medicament or vaccine may also comprise a variant of said recombinant single-chain alpha-hemolysin polypeptide, wherein in addition to said deletion in the stem domain and said insertion of heterologous sequence, 1 to 50 amino acid residues are added, substituted or deleted in respect to the wild-type sequence SEQ ID NO: 1 and has the activity to form oligomers and to bind to lipidic layers, including lipidic mono layers and lipidic bilayers, or cell membranes. In a further preferred embodiment the variant of said recombinant single-chain alpha-hemolysin polypeptide preferably has 1 to 40, further preferred 1 to 25 amino acid residues, still further preferred 1 to 20 amino acid residues, even further preferred 1 to 15 amino acid residues, particularly preferred 1 to 10 amino acid residues and most preferred 1 to 5 amino acid residues, which are added, substituted or deleted in respect to the wild-type sequence SEQ ID NO: 1, in addition to said deletion in the stem domain and said insertion of heterologous sequence and has the activity to form oligomers and to bind to lipidic layers, including lipidic mono layers and lipidic bilayers, or cell membranes.

The synthesis of a multivalent vaccine as a single protein by using an antigen of the targeted pathogen as a carrier protein is advantageous to prevent the pathogenesis of complex infectious agents such as *S. aureus* by inducing humoral and/or cellular immune responses.

According to the invention the recombinant single-chain alpha-hemolysin polypeptide may be used for the preparation of antibodies. When using the recombinant single-chain alpha-hemolysin polypeptide for the preparation of antibodies, preferably a mixture of antibodies is obtained comprising antibodies directed to alpha-hemolysin and antibodies directed to the respective heterologous sequence or sequences. In case a passive immunization with a mixture of antibodies against a disease caused by *Staphylococcus* is desired the heterologous sequence or sequences all are derived from *Staphylococcus*.

In an alternative method antibodies directed to different antigens may be separated. Further, monoclonal antibodies may also be prepared according to methods well-known for the person skilled in the art.

The recombinant single-chain alpha-hemolysin polypeptide according to the present invention may also be used in assays for detecting and/or selecting an agent binding to the heterologous sequence, preferably for detecting antibodies directed to the heterologous sequence. The recombinant polypeptide therefore is suitable to screen for ligands, for example finechemicals, peptides or proteins, which bind to the heterologous sequence. The recombinant polypeptide is also suitable for epitope mapping. A further application is the use of the recombinant polypeptide for detecting antibodies in a sample, e.g. blood or serum sample, which antibody is directed to the heterologous sequence. In such an assay the recombinant alpha-hemolysin polypeptide according to the present invention may be bound to a liposome which is bound to a solid support. The binding of the liposome to a solid support may be preferably achieved by avidin/strepavidin binding. A suitable solid support may be the surface of a well of a multi-well plate.

The advantages of the recombinant polypeptide according to the present invention is that:

(i) Polypeptides can be overproduced which are difficult to express.

(ii) One to several heterologous polypeptides may be displayed simultaneously in a single protein; wherein the display is performed in fusion and into solvent-exposed loops of a carrier protein (alpha hemolysin according to the invention).

(iii) Multivalent antigens can be designed that can be used in vaccinal preparations, particularly for the preventive and/or therapeutic treatment of diseases caused by *Staphylococcus*.

(iv) Multivalent antigens can be designed that can be used as antigenic sources for antibody development and preparation.

(v) Antibody production against heterologous polypeptides corresponding to native epitopes and/or mimotopes can be elicited.

(vi) A system is provided for an oriented immobilisation of proteins at the surface of liposomes or any types of lipidic layers, for studying protein interactions by using diverse techniques such as ELISA, Biacore, Biosensor. The immobilisation of proteins at the surface of liposomes is due to the interaction of the carrier moiety (alpha-hemolysin) with lipidic layer such as liposomes. This system is also promising when using liposomic adjuvant in vaccinology and antibody developments.

Further, the recombinant polypeptide of the present invention may be used for display of randomized protein fragment libraries. The parent domain (alpha hemolysin as constructed according to the present invention) can serve as a scaffold to display random protein fragment libraries. The heterologous protein or polypeptide fragments are expected to be conformationally constrained, stabilized and protected against proteolysis. By using phage display, bacterial display, ribosome display and yeast display, this approach can be used for making antigen fragment libraries and mapping epitopes recognised by monoclonal and polyclonal antibodies. The recombinant polypeptide of the present invention constitutes an original tool not only for epitope mapping but also in immunoassay development.

In addition, the recombinant alpha-hemolysin polypeptide as a single-chain protein is less costly to manufacture and has the advantage of a practical production process and more straightforward quality control testing than a vaccine consisting of several recombinant proteins. Therefore, the recombinant alpha-hemolysin polypeptide is particularly useful as medicament and vaccine.

An alternative embodiment of the present invention is directed to a recombinant single-chain alpha-hemolysin polypeptide of *Staphylococcus aureus*, having a deletion in the stem domain for removing hemolytic activity, containing a fragment of the immunoglobulin G-binding domain of protein A of *Staphylococcus* species, preferably of *Staphylococcus aureus* inserted into a permissive site. As explained in the following said fragment of the immunoglobulin G-binding domain of protein A is having a minimum size of 5 amino acid residues and has no or reduced binding activity to Fc or Fab domain of immunoglobulin G compared to full-length protein A.

*Staphylococcal* protein A (SpA) plays a key role in the pathogenicity of *S. aureus*. SpA is a protein of 42 kDa and comprises several regions with different functions (FIG. 14): the repeat region Wr, which are used for spa typing, the We region, which confers anchoring to the bacterial cell wall, the signal sequence (S region) in the N-terminal part and the four or five highly homologous immunoglobulin G (IgG)-binding domains, designated E, D, A, B, and C which share 65-90% amino acid sequence identity (FIG. 15). The Z domain of SpA reported in literature is an engineered analogue of the IgG-binding domain B. The size of these domains is relatively small; each contains ~58 amino acid residues. The solution structures of two of these domains, the B and E domains, as well as the very similar Z domain, have been determined by NMR spectroscopy. These structural analyses revealed that these IgG-binding domains adopted a classical "up-down" three-helical bundle fold. Cristallography and NMR studies indicated that the helix 1 and helix 2 interact with the Fc part of Ig while helix 2 and helix 3 bind to the Fab domain of Ig. These studies also indicated that the binding activity of SpA Ig-binding domains requires the presence of the three helices and is dependent of its 3D structure.

The binding activity of SpA acts to cloak the bacterial cell with IgG, thus blocking any interaction with Fc receptors on neutrophils and hindering phagocytosis. As well as binding the Fc region of IgG, each individual SpA domain also interacts with VH3 Fab fragments of many IgM, IgA, IgG, and IgE molecules via the heavy chain, although this does not interfere with the antibody's antigen-binding site. Because of this ability to bind to Fab, SpA acts as a B-cell superantigen, inducing proliferation and subsequent depletion of the B-cell repertoire. SpA-bound IgG also inhibits complement fixation by the classical pathway.

The use of SpA as candidate for a vaccine against the *S. aureus* infections was never used in the past. The problems related to the use of SpA in a vaccine preparation are related to the capacity of SpA to bind the Fc part of immunoglobulins and thus to escape the immune system and to cause a depletion of the B-cell repertoire. Immunization assays performed by the present inventors by using ICHA I 009 confirmed that the display of a functional Ig-binding domain of SpA into ICHA did not trigger the induction of anti-SpA antibodies (data not shown).

Another problem related to the use of functional SpA Ig-binding domain in human vaccine is the risk to cause an anti-idiotypic response which is characterised by the apparition of auto-antibodies. This occurs when the paratope of the anti-SpA antibodies stimulates the immune system to generate secondary antibodies which display a paratope that mimics the structural and biological properties of the antigen.

Anti-idiotypic antibodies recognize the idiotypic determinants (paratope) expressed in the variable region of a particular antibody or the variable regions of a group of related antibodies. It has been proposed that anti-idiotypic antibodies are expressed in order to regulate the expression of antibodies that dominate the response to a particular antigen. Suppression of B cells expressing these dominant antibodies would allow for the proliferation of other antibodies using alternative variable region sequences and ultimately to the diversification of the antibody response. While the expression of anti-idiotypic antibodies would normally decline with the decreased expression of the antibodies to which they are responding, anti-idiotypic antibodies that cross-react with something so ubiquitous as self-IgG have the potential to be continually propagated.

Therefore a further objection of the present invention was to provide an vaccine on the basis of protein A which does not involve the drawbacks of the state of art.

The present invention therefore also provides a recombinant single-chain alpha-hemolysin polypeptide of Staphylococcus aureus, having a deletion in the stem domain for removing hemolytic activity, wherein at least one heterologous sequence is inserted into a permissive site, and wherein the heterologous sequence comprises a fragment of the immunoglobulin G-binding domain of protein A of Staphylococcus species, preferably of *Staphylococcus aureus;* wherein said fragment of the immunoglobulin G-binding domain of protein A is having a minimum size of 5 amino acid residues and has no or reduced binding activity to Fc or Fab domain of immunoglobulin G compared to full-length protein A;

or a variant thereof, wherein in addition to said deletion in the stem domain and said insertion of heterologous sequence, 1 to 50 amino acid residues are added, substituted or deleted in respect to the wild-type sequence SEQ ID NO: 1 and has the activity to form oligomers and to bind to lipidic bilayers, including lipidic mono layers and lipidic bilayers, or cell membranes.

In a further preferred embodiment of the present invention said fragment of the immunoglobulin G-binding domain of protein A has no or reduced binding activity to Fc and has no or reduced binding activity to Fab domain of immunoglobulin G compared to full-length protein A. In a particularly preferred embodiment of the present invention said fragment of the immunoglobulin G-binding domain of protein A has no significant binding activity to Fc and has no significant binding activity to Fab domain of immunoglobulin G.

Since the SpA's capacity to interact with the Fc or the Fab region of immunoglobulin molecules is strongly reduced or abolished in the recombinant alpha-hemolysin polypeptide of the present invention, the above mentioned drawbacks can be overcome and antibodies can be raised against Staphylococcus antigens, particularly directed against Staphylococcus protein A antigen, and mammals can be vaccinated against Staphylococcus much more effectively.

As mentioned above the deletion in the stem domain or the insertion of heterologous sequences into the mentioned insertion sites do not abolish the activity to form oligomers or to bind to lipidic layers, including lipidic mono layers and lipidic bilayers, or cell membranes.

In a preferred embodiment of the present invention the fragment of the immunoglobulin G-binding domain of protein A is having a minimum length of 5 amino acid residues, preferably at least 8, at least 10, at least 12, at least 15, at least 20, at least 25, at least 30 amino acid residues.

In a further preferred embodiment of the invention the fragment of the immunoglobulin G-binding domain of protein A is having a length of 5 to 35 amino acid residues, preferably 5 to 30 amino acid residues, further preferred 10 to 30 amino acid residues, and even further preferred 10 to 25 amino acid residues.

Further preferred, the fragment of the immunoglobulin G-binding domain of protein A covers not more than two complete alpha-helices.

The selection of a certain limited size of the fragment of the immunoglobulin G-binding domain of protein A makes sure that the fragment does not have a significant Fab or Fc binding activity. As mentioned above, the binding activity of protein A immunoglobulin G binding domains requires the presence of the three alpha-helices (helix 1, helix 2 and helix 3). For the purpose to develop a vaccine against Staphylococcus the fragment of the immunoglobulin G-binding domain of protein A shall have no significant Fab or Fc binding activity. The person skilled in the art will be able to chose fragments of protein A immunoglobulin G binding domains for insertion into the detoxified HA molecule so that said fragment will have no significant Fab or Fc binding activity, e.g. by choosing a fragment covering not more than one or two complete helices of the three-helical bundle fold (helix 1, helix 2 and helix 3).

In a further preferred embodiment the fragment of protein A immunoglobulin G binding domains comprises the sequence of not more than one complete helix selected from helix 1, helix 2 and helix 3 of the immunoglobulin G (IgG)-binding domains E, D, A, B, and C.

In yet another particularly preferred embodiment the fragment of protein A is selected from sequences SEQ ID NOs: 16 to 18 (see table 2).

In another preferred embodiment the permissive site is located within an solvent-exposed loop, preferably selected from the group consisting of regions defined by amino acid position 108 to 151, amino acid position 1 to 5, amino acid position 288 to 293, amino acid position 43 to 48, amino acid position 235 to 240, amino acid position 92 to 97, amino acid position 31 to 36, amino acid position 156 to 161 in respect to the wild-type sequence SEQ ID NO: 1.

As used herein the term "solvent-exposed loop" means that the respective part of the amino acid sequence of alpha-hemolysin polypeptide, which is forming a loop, is exposed to and accessible from an aqueous medium or biological fluids such a blood.

A further preferred embodiment of the present invention is that permissive site of the alpha-hemolysin polypeptide is located in a region selected from the group consisting of regions defined by amino acid position 108 to 151 (site 1), amino acid position 43 to 48 (site 4), amino acid position 235 to 240 (site 5), amino acid position 92 to 97 (site 6), amino acid position 31 to 36 (site 7), amino acid position 156 to 161 (site 8) in respect to the wild-type sequence SEQ ID NO: 1.

In an even further preferred embodiment the alpha-hemolysin polypeptide comprises said heterologous sequence inserted in a region defined by amino acid position 108 to 151 (site 1) in respect to the wild-type sequence SEQ ID NO: 1.

As mentioned above, the recombinant alpha-hemolysin polypeptide according to the invention has a deletion in the stem domain: this deletion in the stem domain serves the purpose to abolish toxicity of the alpha-hemolysin and is achieved by that the polypeptide does not anymore form a pore in the cell membrane. The stem domain lies within the amino acid sequence from Thr109 to Gln150 in respect to the wild-type sequence SEQ ID NO: 1. In a preferred embodiment the amino acid sequence from Thr109 to Gln150 in respect to the wild-type sequence SEQ ID NO: 1 is partially or completely removed. Further preferred, the amino acid sequence from Thr109 to Gln150 in respect to the wild-type sequence SEQ ID NO: 1 is completely removed.

Further preferred, the region (Thr109 to Gln150) which includes the stem region (K110 to Y148) and some amino acids of the triangle region, has been substituted with the tripeptide PGN (see table 1). The nucleotide sequence of the tripeptide is used to create an insertion site of heterologous polypeptides in the nucleotidic sequence of the alpha hemolysin encoding gene. As a result, the protein loses its hemolytic activity. The region Thr109 to Gln150 of alpha-hemolysin is very suitable for insertion and display of large polypeptides. This is because the substitution of this region does not damage the other biological activities of the protein (correct folding, binding to lipidic layer, oligomer formation). In regard to the 3D structure, the present inventors found that the stem domain and thus the insertion site are flanked with a natural linker which corresponds to the triangle region. This region spaces the core of the protein to the stem domain so that they have a folding which is independent to the other.

In yet another preferred embodiment the alpha-hemolysin moiety is having the sequence SEQ ID NO: 3 (ICHA I) or SEQ ID NO: 5 (ICHA II), or variants thereof wherein the alpha-hemolysin moiety has 85%, preferably 90%, further preferred 95% or more amino acid identity in respect to the sequences SEQ ID NO: 3 or SEQ ID NO: 5.

The present invention also provides a polynucleotide encoding the recombinant recombinant single-chain alpha-hemolysin polypeptide of Staphylococcus aureus, having a deletion in the stem domain for removing hemolytic activity, wherein at least one heterologous sequence is inserted into a permissive site, and wherein the heterologous sequence comprises a fragment of the immunoglobulin G-binding domain of protein A of *Staphylococcus* species, preferably of *Staphylococcus aureus;* wherein said fragment of the immunoglobulin G-binding domain of protein A is having a minimum size of 5 amino acid residues and has no or reduced binding activity to Fc or Fab domain of immunoglobulin G compared to full-length protein A; or a variant thereof, wherein in addition to said deletion in the stem domain and said insertion of heterologous sequence, 1 to 50 amino acid residues are added, substituted or deleted in respect to the wild-type sequence SEQ ID NO: 1 and has the activity to form oligomers and to bind to lipidic bilayers, including lipidic mono layers and lipidic bilayers, or cell membranes.

The present invention also refers to a vector comprising said polynucleotide and to a transformant comprising said polynucleotide or said vector.

The recombinant polypeptide can be used in prevention and/or therapy caused by *Staphylococcus* spec. particularly of *Staphylococcus aureus*. The polynucleotide or the vector as mentioned above can be used in DNA vaccination.

Further, the present invention provides a medicament or vaccine comprising a recombinant single-chain alpha-hemolysin polypeptide of *Staphylococcus aureus*, having a deletion in the stem domain for removing hemolytic activity, wherein at least one heterologous sequence is inserted into a permissive site, and wherein the heterologous sequence comprises a fragment of the immunoglobulin G-binding domain of protein A of *Staphylococcus* species, preferably of *Staphylococcus aureus;* wherein said fragment of the immunoglobulin G-binding domain of protein A is having a minimum size of 5 amino acid residues and has no or reduced binding activity to Fc or Fab domain of immunoglobulin G compared to full-length protein A;
or a variant thereof, wherein in addition to said deletion in the stem domain and said insertion of heterologous sequence, 1 to 50 amino acid residues are added, substituted or deleted in respect to the wild-type sequence SEQ ID NO: 1 and has the activity to form oligomers and to bind to lipidic bilayers, including lipidic mono layers and lipidic bilayers, or cell membranes.

In a further preferred embodiment of the medicament of present invention said fragment of the immunoglobulin G-binding domain of protein A has no or reduced binding activity to Fc and has no or reduced binding activity to Fab domain of immunoglobulin G compared to full-length protein A. In a particularly preferred embodiment of the present invention said fragment of the immunoglobulin G-binding domain of protein A has no significant binding activity to Fc and has no significant binding activity to Fab domain of immunoglobulin G.

DETAILED DESCRIPTION OF THE EMBODIMENTS

The invention is related to the development of an engineered form of the *staphylococcal* alpha-hemolysin (HA), termed ICHA for Inactivated Carrier Hemolysin Alpha. The ICHA encoding gene was obtained by insertion of numerous restriction sites in the coding sequence of the Hemolysin Alpha (HA) and by substitution of the nucleotidic sequence coding for the HA fragment Thr109-Gln150 with an additional restriction site. The resulting protein loses its haemolytic activity but is still able to interact with lipidic layers, to form oligomer and to induce neutralizing antibodies against HA. The restriction sites created in the ICHA encoding gene corresponds to permissive insertion sites that are used to display at least one heterologuous polypeptide at the surface of the carrier protein. The heterologuous polypeptides can be display in fusion with ICHA or into ICHA. The displayed polypeptides can be peptides, protein fragments or proteins.

As used herein the term "heterologous sequence" refers to any amino acid sequence other than alpha-hemolysin sequence. The "heterologous sequence" or "heterologous sequences" may be of any origin including virus, bacteria, plant, fungi, parasite, animal or human or even an arbitrary artificial sequence. In a particularly preferred embodiment the heterologous sequence or heterologous sequences is/are exclusively derived from *Staphylococcus* species, preferably *Staphylococcus aureus*. The heterologous sequence could correspond to B-cell or T-cell epitopes. It also includes mimotopes, peptide, which mimics the structure of an epitope. Because of this property it causes an antibody response identical to the one elicited by the native epitope. In this case, This native epitope could also correspond to macromolecules which are not related to protein such as peptidoglycan, teichoic acid, lipoteichoic acid, capsular polysaccharide.

As used herein the term "permissive site" means that insertion of a sequence in such a permissive site does not significantly alter the characteristics and activity of the alpha-hemolysin polypeptide construct as defined in the present invention (with hemolytic activity being removed). Here the permissive site preferably is located within an solvent-exposed loop, which further preferred is selected from the group consisting of regions defined by amino acid position 108 to 151, amino acid position 1 to 5, amino acid position 288 to 293, amino acid position 43 to 48, amino acid position 235 to 240, amino acid position 92 to 97, amino acid position 31 to 36, amino acid position 156 to 161 in respect to the wild-type sequence SEQ ID NO: 1.

As used herein the term "solvent-exposed loop" means that the respective part of the amino acid sequence of alpha-hemolysin polypeptide, which is forming a loop, is exposed to and accessible from an aqueous medium or biological fluids such a blood.

Production of the Polypeptides of the Invention

The polypeptides of the current invention can, for example, be produced using recombinant methods and techniques known in the art. Although specific techniques for their preparation are described herein, it is to be understood that all appropriate techniques suitable for production of these polypeptides are intended to be within the scope of this invention.

Generally, these techniques include DNA and protein sequencing, cloning, expression and other recombinant engineering techniques permitting the construction of prokaryotic and eukaryotic vectors encoding and expressing each of the peptides of the invention.

The polypeptides of the invention may be produced by expression of a nucleic acid (polynucleotide) encoding the polypeptide of interest. Expression of the encoded polypeptides may be done in bacterial, yeast, plant, insect, or mammalian hosts by techniques well known in the art. The polypeptides could be also obtained by chemical synthesis or by in vitro transcription/translation using cell-extracts or purified proteins of the transcription/translation machineries.

In an embodiment, a polypeptide of interest of the invention is obtained by cloning the DNA sequence into a vector. A host cell is transformed with the modified nucleic acid to allow expression of the encoded polypeptide.

Methods for cloning DNA into a vector and for inserting, deleting and modifying polynucleotides and for site directed mutagenesis are described, for example, in *Promega Protocols and Applications Guide*, supra. Cells or bacteria may be transfected with a vector, preferably with an expression vector, having the desired DNA sequence attached thereto, by known techniques including heat shock, electroporation, calcium phosphate precipitation and lipofection, among others. The terminal peptides or other analogues or fragments may then be extracted and purified by, for example, high pressure liquid chromatography (HPLC), ion exchange chromatography or gel permeation chromatography. However, other methods and techniques known in the art of conducting the different steps or combinations of these steps necessary to derive the peptide of this invention or equivalent steps are contemplated to be within the scope of this invention.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. U.S.A.* 85:2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

Nucleic Acids of the Invention

Also provided herein are isolated nucleic acids that comprise DNA or RNA sequences (polynucleotides) encoding the peptides of the invention. The nucleic acids of the invention may further comprise vectors for expression of the peptides of the invention. It is understood by one of ordinary skill in the art that because of degeneracy in the genetic code, substitutions in the nucleotide sequence may be made which do not result in changes in the encoded amino acid sequence. It is further understood by one of ordinary skill in the art that both complementary strands of any DNA molecule described herein are included within the scope of the invention.

As used herein, the term "vector" refers to a vehicle made of a polynucleotide or which contains a polynucleotide which can transfer a polynucleotide sequence or gene of interest to a target cell. The vector may be a "viral vector" or a "plasmid vector" or may combine both properties in one construct. Examples of a vector include vectors which are capable of self replication or capable of being incorporated into a chromosome within host cells (e.g., prokaryotic cells, yeast, animal cells, plant cells, insect cells, whole animals, and whole plants), and contain a promoter at a site suitable for transcription of a polynucleotide or gene.

As used herein, the term "expression vector" refers to a nucleic acid sequence comprising a structural gene and a promoter for regulating expression thereof, and in addition, various regulatory elements in a state that allows them to operate within host cells. The regulatory element may include, preferably, terminators, selectable markers such as drug-resistance genes (e.g., a kanamycin resistance gene, a hygromycin resistance gene, etc.), and enhancers. It is well known to those skilled in the art that the type of an organism, expression vector and the type of a regulatory element may vary depending on the host cell.

As used herein, the term "promoter" refers to a base sequence which determines the initiation site of transcription of a gene and is a DNA region which directly regulates the frequency of transcription. Transcription is started by RNA polymerase binding to a promoter.

As used herein, the terms "transformation", "transduction" and "transfection" are used interchangeably unless otherwise mentioned, and refers to introduction of a nucleic acid into host cells. As a transformation method, any technique for introducing DNA into host cells can be used, including various well-known techniques, such as, for example, the electroporation method, the particle gun method (gene gun), the calcium phosphate method, and the like.

As used herein, the term "transformant" refers to the whole or a part of an organism, such as a cell, which is produced by transformation. Examples of a transformant include prokaryotic cells, such as bacteria (e.g. *Escherichia coli*), yeast, animal cells, plant cells, insect cells and the like. Transformants may be referred to as transformed cells, transformed tissue, transformed hosts, or the like, depending on the subject. As used herein, all of the forms are encompassed, however, a particular form may be specified in a particular context.

Vaccines

Vaccines of the invention may also comprise a pharmaceutically acceptable carrier. A pharmaceutically acceptable carrier is a material that can be used as a vehicle for the antigen because the material is inert or otherwise medically acceptable, as well as compatible with the active agent, in the context of vaccine administration. In addition to a suitable excipient, a pharmaceutically acceptable carrier can contain conventional vaccine additives like diluents, adjuvants and other immunostimulants, antioxidants, preservatives and solubilizing agents. For example, polysorbate 80 may be added to minimize aggregation and act as a stabilizing agent, and a buffer may be added for pH control.

Methods for making vaccines are generally known in the art. In addition, the vaccines of the present invention may be formulated so as to include a "depot" component to increase retention of the antigenic material at the administration site. By way of example, in addition to an adjuvant (if one is used), alum (aluminum hydroxide or aluminum phosphate), QS-21, dextran sulfate or mineral oil may be added to provide this depot effect.

The present invention also provides a method of treating or preventing an infection by administering any of the above-described vaccines to a subject in need thereof. A target subject population for the treatment and prevention methods described herein includes mammals, such as humans/bovines/pigs, who are infected with, or at risk of being infected by, bacterial pathogens, such a S. aureus. In some embodiments, the infection to be treated or prevented is associated with a methicillin-resistant S. aureus. In particular embodiments, the methicillin-resistant S. aureus produces alpha-toxin.

A therapeutically or prophylactically effective amount of the inventive vaccines can be determined by methods that are routine in the art. Skilled artisans will recognize that the amount may vary with the composition of the vaccine, the particular subject's characteristics, the selected route of administration, and the nature of the bacterial infection being treated or prevented. General guidance can be found, for example, in the publications of the International Conference on Harmonization and in REMINGTON'S PHARMACEUTICAL SCIENCES (Mack Publishing Company 1990). A typical vaccine dosage may range from 1 µg -400 µg of antigen.

The vaccine may be administered with or without an adjuvant. If an adjuvant is used, it is selected so as to avoid adjuvant-induced toxicity. For example, a vaccine according to the present invention may comprise a f3-glucan as described in U.S. Pat. No. 6,355,625, or a granulocyte colony stimulating factor.

The vaccine may be administered in any desired dosage form, including dosage forms that may be administered to a mammal intravenously, intramuscularly, or subcutaneously. The vaccine may be administered in a single dose, or in accordance with a multi-dosing protocol. Administration may be by any number of routes, including subcutaneous, intracutaneous, and intravenous. In one embodiment, intramuscular administration is used. The skilled artisan will recognize that the route of administration will vary depending on the bacterial infection to be treated or prevented and the composition of the vaccine.

The vaccine may be administered in conjunction with an anti-infective agent, an antibiotic agent, and/or an antimicrobial agent, in a combination therapy. Exemplary anti-infective agents include, but are not limited to vancomycin and lysostaphin. Exemplary antibiotic agents and antimicrobial agents include, but are not limited to penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin, imipenem, meropenem, gentamycin, teicoplanin, lincomycin and clindamycin. The anti-infective, antibiotic and/or antimicrobial agents may be combined prior to administration, or administered concurrently or sequentially with the vaccine composition.

Antibodies

The invention also refers to the preparation of antibodies. The present invention further provides compositions comprising antibodies that specifically bind to an S. aureus alpha-hemolysin antigen and antibodies that specifically bind to the heterologous sequence(s). The antibodies may be monoclonal antibodies, polyclonal antibodies, antibody fragments or any combination thereof. The antibodies may be formulated with a pharmaceutically acceptable carrier.

The term "antibody," as used herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, including an antibody fragment. "Antibody" and "immunoglobulin" are used synonymously herein. An antibody fragment is a portion of an antibody such as F(ab')2, F(ab)2, Fab', Fab, Fv, sFv, Nanobodies and the like. Nanobodies are antibody-derived therapeutic proteins that contain the unique structural and functional properties of naturally-occurring heavy-chain antibodies. The Nanobody technology was originally developed following the discovery that camelidae (camels and llamas) possess fully functional antibodies that lack light chains. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. The antibodies could be obtained using immunization in human and animals (mouse, rabbit, camel, lama, hen, goat).

Regardless of structure, an antibody fragment binds with the same antigen that is recognized by the full-length antibody, and, in the context of the present invention. Methods of making and screening antibody fragments are well-known in the art.

An anti-alpha-hemolysin antibody or antibodies directed to the homolgous sequence which can be obtained according to the present invention may be prepared by a number of different methods. For example, the antibodies may be obtained from subjects administered the recombinant polypeptide according to the present invention. The antibodies also may be obtained from plasma screened for alpha-toxin antibodies and/or bacterial antigen antibodies, as discussed in more detail below. In some embodiments, the antibodies may be made by recombinant methods. Techniques for making recombinant monoclonal antibodies are well-known in the art. Recombinant polyclonal antibodies can be produced by methods analogous to those described in U.S. Patent Application 2002/0009453, using the recombinant polypeptide according to the present invention as the immunogen(s). Said antibody obtained in accordance with the invention may be a murine, human or humanized antibody. A humanized antibody is a recombinant protein in which the CDRs of an antibody from one species; e.g., a rodent, rabbit, dog, goat, horse, camel, lama or chicken antibody (or any other suitable animal antibody), are transferred from the heavy and light variable chains of the rodent antibody into human heavy and light variable domains. The constant domains of the antibody molecule are derived from those of a human antibody. Methods for making humanized antibodies are well known in the art. More recently, it was reported that it is possible to generate hybridomas directly from human B-cells. Consequently, the recombinant polypeptide according to the present invention could be used to stimulate proliferation of human B-cell before to proceed to the generation of hybridomas.

The above-described antibodies can be obtained by conventional methods. For example, the recombinant polypeptide according to the present invention can be administered to a subject and the resulting IgGs can be purified from plasma harvested from the subject by standard methodology.

Antibody Compositions

The invention also refers to the preparation of antibodies and antibody compositions suitable for administration, such as compositions comprising an antibody and a pharmaceutically acceptable carrier. The antibody compositions may be formulated for any route of administration, including intravenous, intramuscular, subcutaneous and percutaneous, by methods that are known in the art. In one embodiment, the antibody composition provides a therapeutically or prophylactically effective amount of antibody, i.e., an amount sufficient to achieve a therapeutically or prophylactically beneficial effect. In a further embodiment, the antibody is a protective antibody composition that neutralizes infection and/or provides protection against infection.

In one embodiment, the antibody composition is an IVIG composition. As used herein, "IVIG" refers to an immunoglobulin composition suitable for intravenous administration. IVIG compositions may contain, in addition to immunoglobulin, a pharmaceutically acceptable carrier. The IVIG compositions may be "specific IVIG," meaning that the IVIG contains immunoglobulins that specifically bind to the antigen(s) represented by the recombinant polypeptide according to the present invention.

In one embodiment, the specific IVIG composition comprises both an antibody that specifically binds to an *S. aureus* alpha-hemolysin antigen (and that optionally neutralizes the alpha-hemolysin antigen) and an antibody that specifically binds to another antigen (and that optionally neutralizes the other antigen), represented by the homologous sequence(s). The antibodies and antigens may be any of those previously described. For example, the other antigen may be SEB (*Staphylococcus aureus* enterotoxin B), TSST (toxic shock syndrome toxine), FnBP (fibronectin-binding protein), BlaZ (β-lactamase), ClfA (Clumping Factor A), PBP2a (penicillin-binding protein 2a), protein A all derived from *Staphylococcus* species, preferably *Staphylococcus aureus*.

Methods of Making IVIG Compositions

The present invention also provides methods of making IVIG compositions, including specific IVIG compositions. An IVIG composition is prepared by administering the recombinant polypeptide according to the present invention to a subject, then harvesting plasma from the subject and purifying immunoglobulin from the plasma.

The subject that is challenged, or administered, the antigen(s), such as the recombinant polypeptide according to the present invention, may be a human or may be another animal, such as a mouse, a rabbit, a rat, a chicken, a horse, a dog, a non-human primate, or any other suitable animal. Antibodies that specifically bind the antigen(s) may be obtained from the animal's plasma by conventional plasma-fractionation methodology.

Antibodies raised against peptides of the invention may also be used to detect the presence of those peptides in various assays. Preferred assays are enzyme immunoassays or radioimmunoassay. The antibodies could be also used to develop affinity chromatography to purify specific proteins or macromolecules.

Treatment and Prevention of Infections with Antibody Compositions

The present invention also refers to a method of treating or preventing infection by administering the above-described antibody compositions, such as the above-described IVIG compositions, to a subject in need thereof. A target patient population for the treatment and prevention of infection includes mammals, such as humans, who are infected with or at risk of being infected by bacterial pathogens. In one embodiment, the infection to be treated or prevented is an *S. aureus* infection, including an infection of methicillin-resistant *S. aureus* or *S. aureus* that produces alpha-toxin, or an *S. epidermidis* infection.

In accordance with one embodiment, the invention provides a method for treating or preventing an *S. aureus* infection using compositions comprising an antibody or antibodies directed to the antigens provided with the recombinant polypeptide according to the present invention, and a pharmaceutically acceptable carrier. In yet another embodiment, the antibodies are monoclonal antibodies.

A therapeutically or prophylactically effective amount of the antibody compositions can be determined by methods that are routine in the art. Skilled artisans will recognize that the amount may vary according to the particular antibodies within the composition, the concentration of antibodies in the composition, the frequency of administration, the severity of infection to be treated or prevented, and subject details, such as age, weight and immune condition, hi some embodiments, the dosage will be at least 50 mg IVIG composition per kilogram of body weight (mg/kg), including at least 100 mg/kg, at least 150 mg/kg, at least 200 mg/kg, at least 250 mg/kg, at least 500 mg/kg, at least 750 mg/kg and at least 1000 mg/kg. Dosages for monoclonal antibody compositions typically may be lower, such as 1/10 of the dosage of an IVIG composition, such as at least about 5 mg/kg, at least about 10 mg/kg, at least about 15 mg/kg, at least about 20 mg/kg, or at least about 25 mg/kg. The route of administration may be any of those appropriate for a passive vaccine. Thus, intravenous, subcutaneous, intramuscular, intraperitoneal and other routes of administration are envisioned. As noted above, a therapeutically or prophylactically effective amount of antibody is an amount sufficient to achieve a therapeutically or prophylactically beneficial effect. A protective antibody composition may neutralize and/or prevent infection. A protective antibody composition may comprise amounts of anti-alpha-hemolysin antibody and/or antibody against the homologous sequence that are not protective on their own, but which, in combination, yield a protective antibody composition.

The antibody composition may be administered in conjunction with an anti-infective agent, an antibiotic agent, and/or an antimicrobial agent, in a combination therapy. Exemplary anti-infective agents include, but are not limited to vancomycin and lysostaphin. Exemplary antibiotic agents and antimicrobial agents include, but are not limited to penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin. imipenem, meropenem, gentamycin, teicoplanin, lincomycin and clindamycin. The anti-infective, antibiotic and/or antimicrobial agents may be combined prior to administration, or administered concurrently or sequentially with the IVIG composition.

In some embodiments, relatively few doses of antibody composition are administered, such as one or two doses, and conventional antibiotic therapy is employed, which generally involves multiple doses over a period of days or weeks. Thus, the antibiotics can be taken one, two or three or more times daily for a period of time, such as for at least 5 days, 10 days or even 14 or more days, while the antibody composition is usually administered only once or twice. However, the different dosages, timing of dosages and relative amounts of antibody composition and antibiotics can be selected and adjusted by one of ordinary skill in the art.

FIGURES

FIG. 1 shows the three-dimensional structure of the heptameric form of alpha-hemolysin (panel A). Panel B shows the monomeric structure in the multimer. Panel C shows a zoomed view of the triangle region. The triangle region, formed by residues Asp103 to Thr109 and Val149 to Asp152, connects the stem domain (residues Lys110 to Tyr148) to the β-sandwich core.

FIG. 2 shows the construction of ICHA, ICHA I and ICHA II. The numbers 1 to 8 correspond to the different protein regions where insertion sites have been created.

FIG. 3 shows the production and purification of HA and ICHA I under denaturing conditions. Panel A shows a COOMASSIE stained SDS-PAGE of samples prepared during the purification of HA. Lane M, molecular weight markers with the size of the proteins indicated; lane TE, supernatant formed from the insoluble fraction containing overexpressed HA; lane IB, inclusion bodies; lane P, purified HA protein by IMAC chromatography. Panel B shows a COOMASSIE stained SDS-PAGE of samples prepared during the purification of ICHA. Lane M: molecular mass marker with the size of the proteins indicated; lane S: soluble fraction isolated from *E. coli* BL21(DE3) transformed with pET28b-ICHA after 4 hours of recombinant protein expression induction with 1 mM IPTG at 37° C.; lane IB: inclusion bodies; lane P: purified ICHA I protein by IMAC chromatography.

Figure 9:
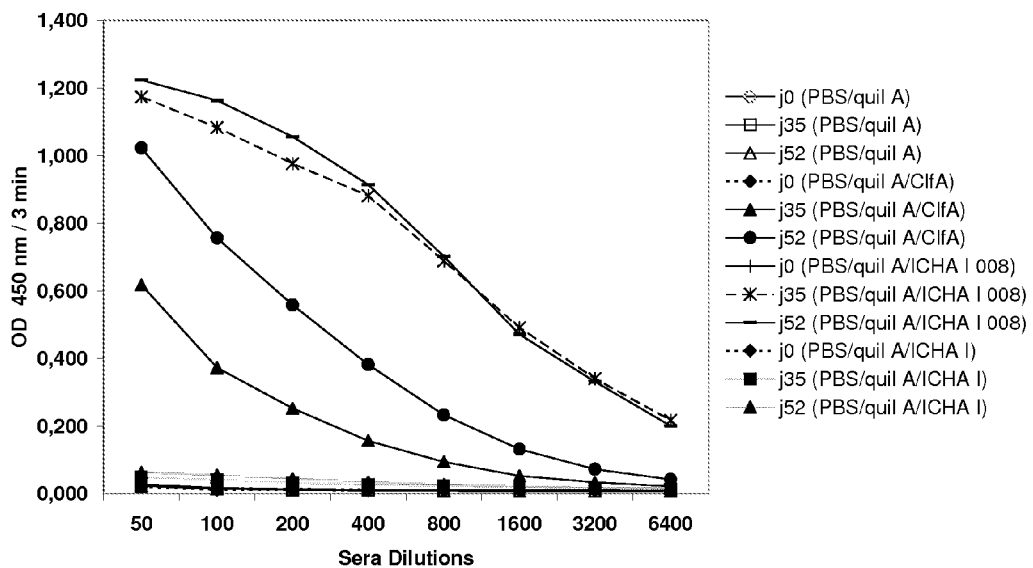
Figure 9:
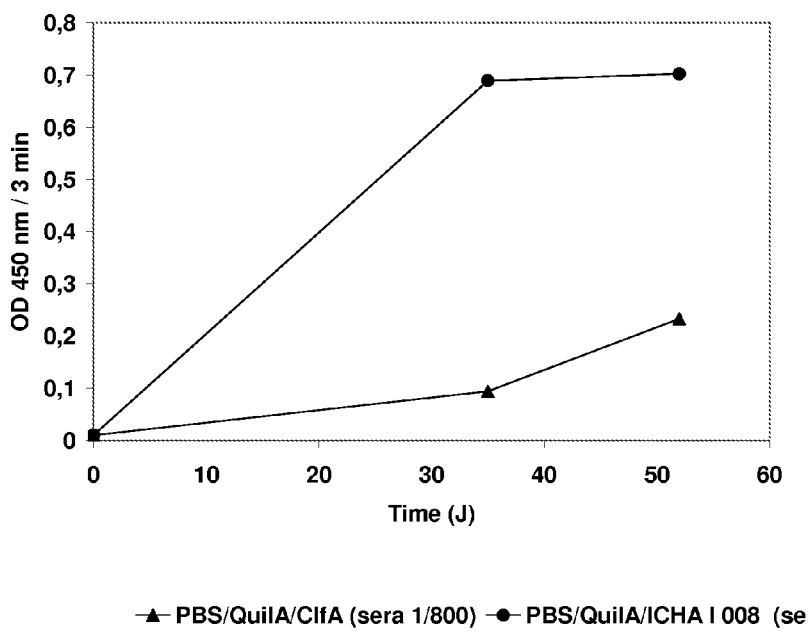
Figure 9:
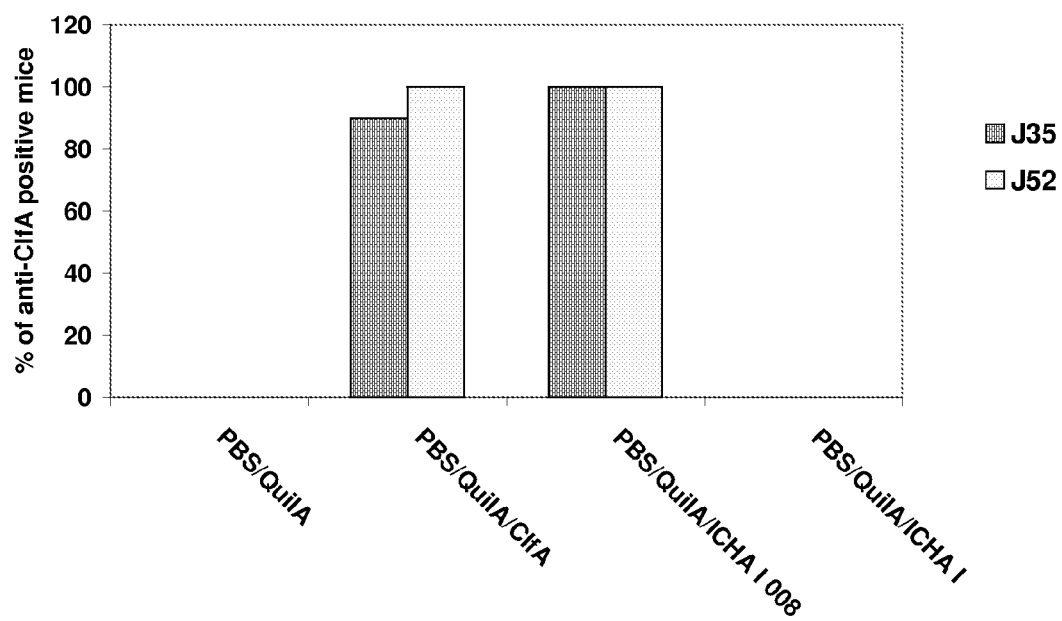

FIG. 9 shows the results in respect to the antibody production against ClfA (501-559) in response to immunizations with ClfA (501-559) and ICHA I 008. The immunizations were performed in BALB/c mice. Panel A corresponds to serotitration curves of total IgG anti-Clfa. Panel B corresponds to the induction kinetic of total IgG anti-Clfa. Panel C describes the percentage of immunized BALB/c mice which develop a positive IgG anti-Clfa response.

Figure 10:
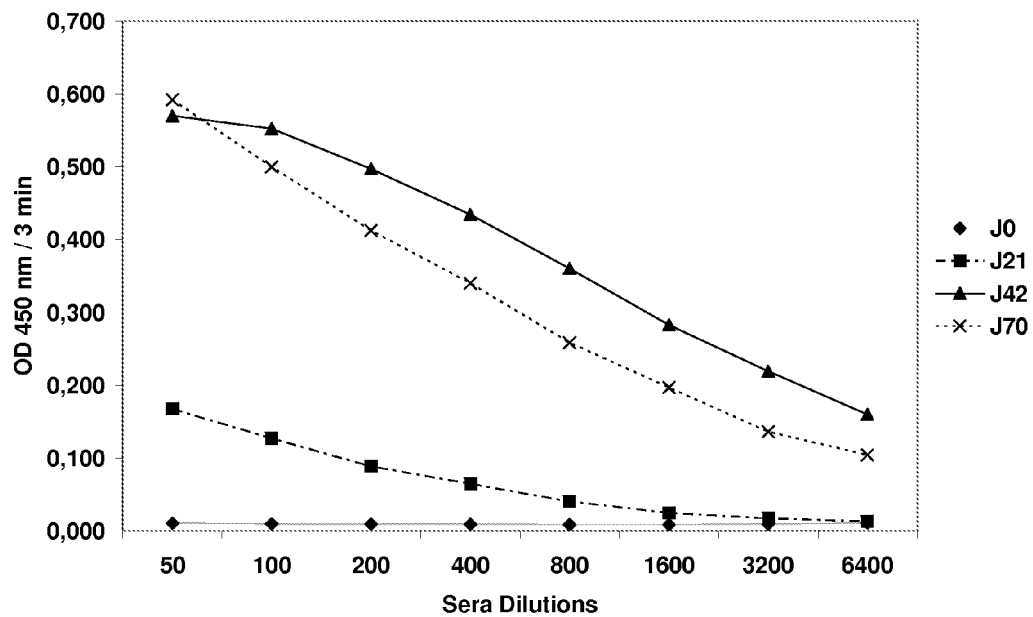
Figure 10:
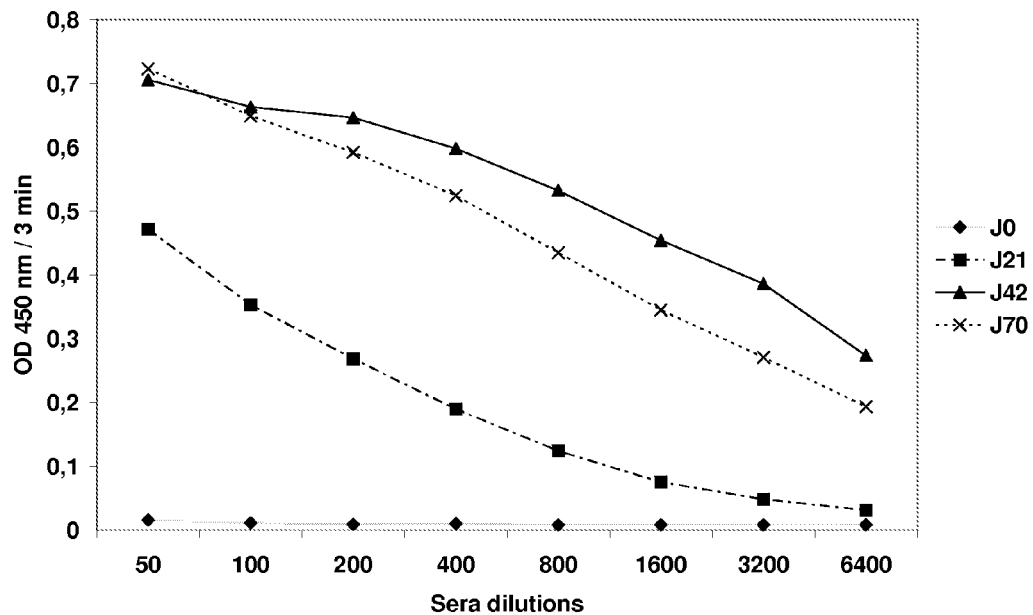
Figure 10:
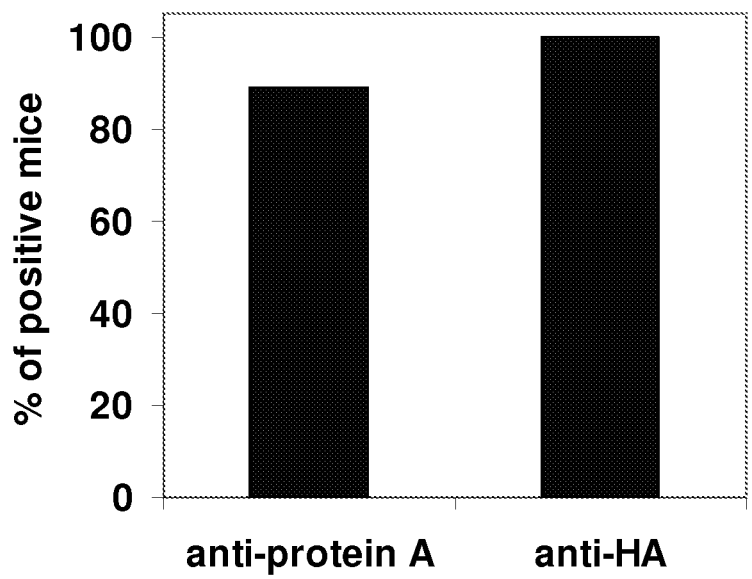

FIG. 10 shows the results in respect to the antibody production against protein A (224-248) in response to immunizations with ICHA I 014. The immunizations were performed in BALb/c mice. Panel A corresponds to serotitration curves of total IgG anti-HA. Panel B corresponds to the induction kinetic of total IgG anti-protein A (224-248). Panel C describes the percentage of immunized BALB/c mice which develop a positive IgG anti-HA and anti-protein A (224-248) response at day 70.

Figure 11:
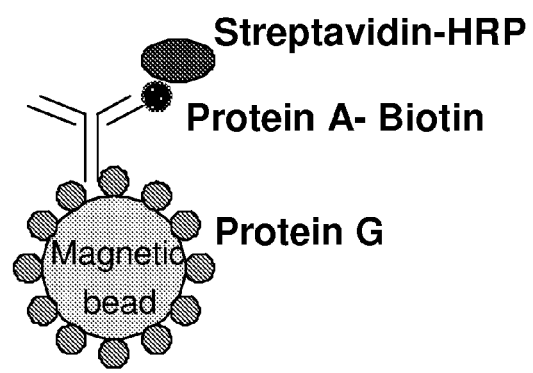
Figure 11:
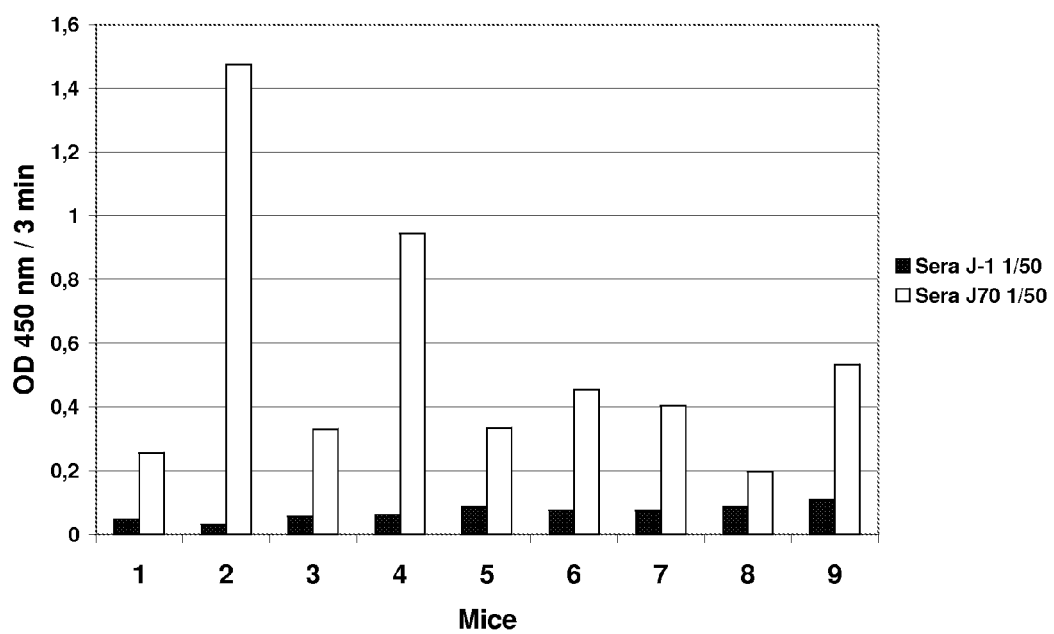

FIG. 11 shows the results in respect to the antibody production against total protein A in response to immunizations with ICHA I 014. The immunizations were performed in BALb/c mice. Panel A describes the technique used to perform the serotitration. Panel B corresponds to the serotitration of total IgG anti-protein A at days 0 and 70.

Figure 12:
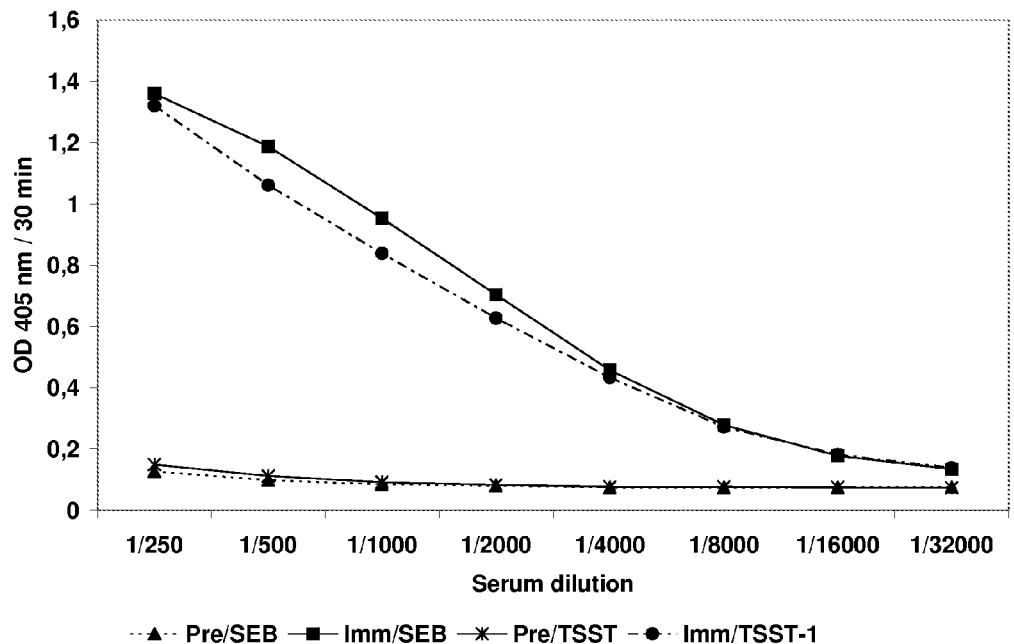
Figure 12:
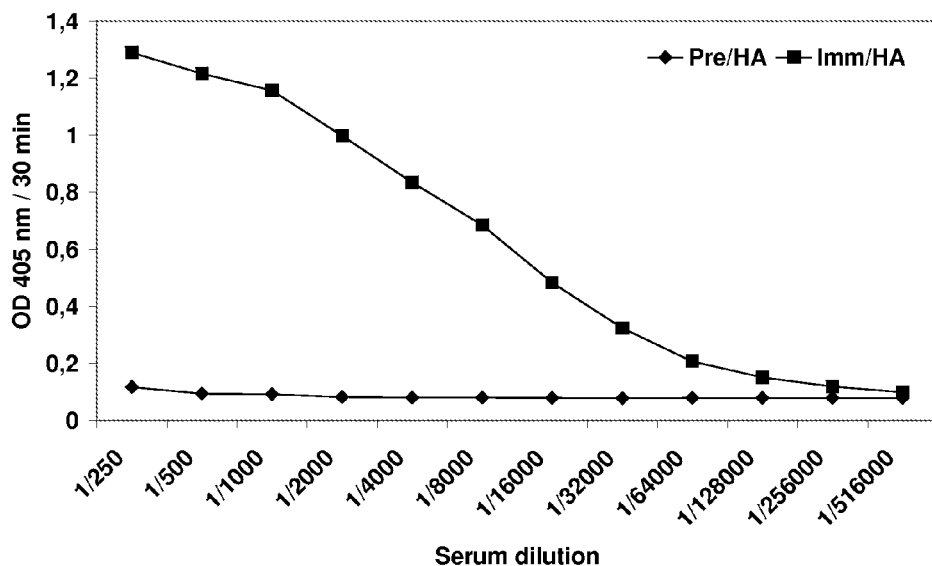

FIG. 12 shows the serotitration of rabbit polyclonal serum obtained after immunization with ICHA I 003. Pre and Imm correspond to the preimmune serum and the serum obtained after 3 injections (day 72), respectively. The serotitrations were realized against HA and two distinct MBP fusion proteins containing either the epitope SEB or the epitope TSST-1.

Figure 4:
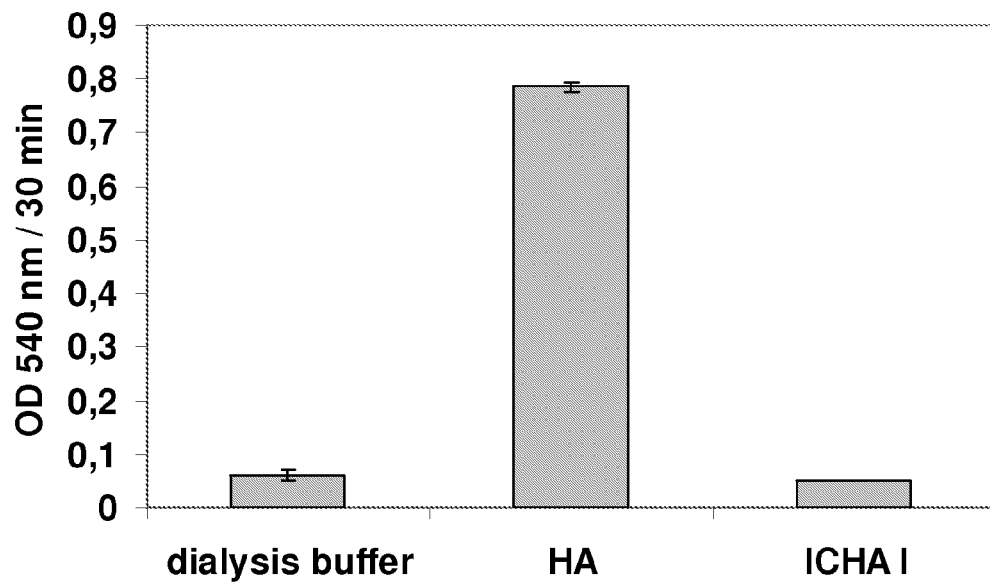
FIG. 4 shows haemolysis assays showing the absence of haemolitic activity of ICHA I, ICHA II.
Figure 4:
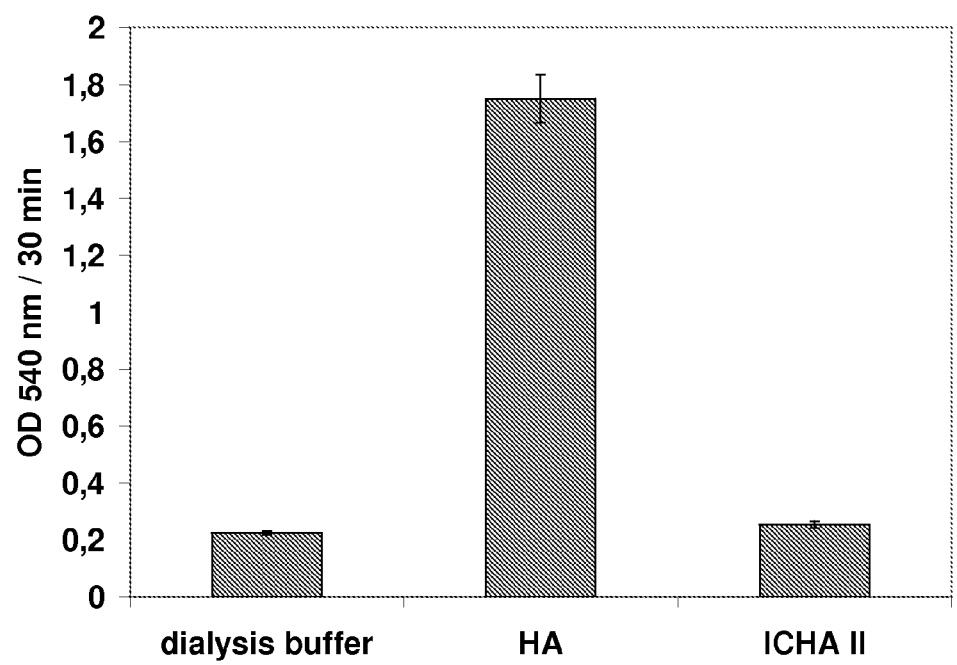
Figure 5:
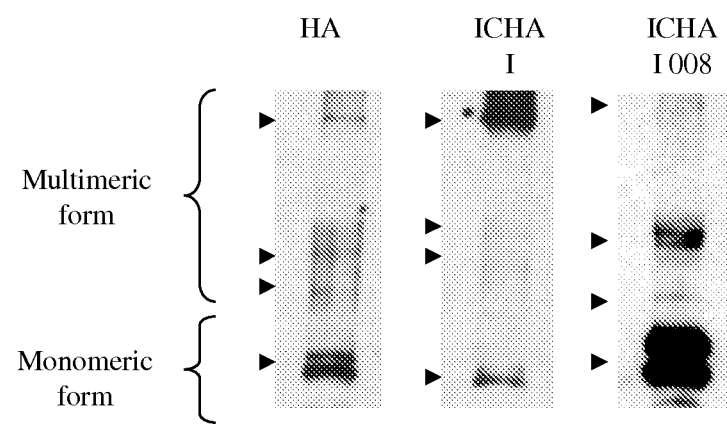
FIG. 5 shows the binding and oligomer formation of HA, ICHA I and ICHA I 008 in the presence of rabbit erythrocytes.
Figure 6:
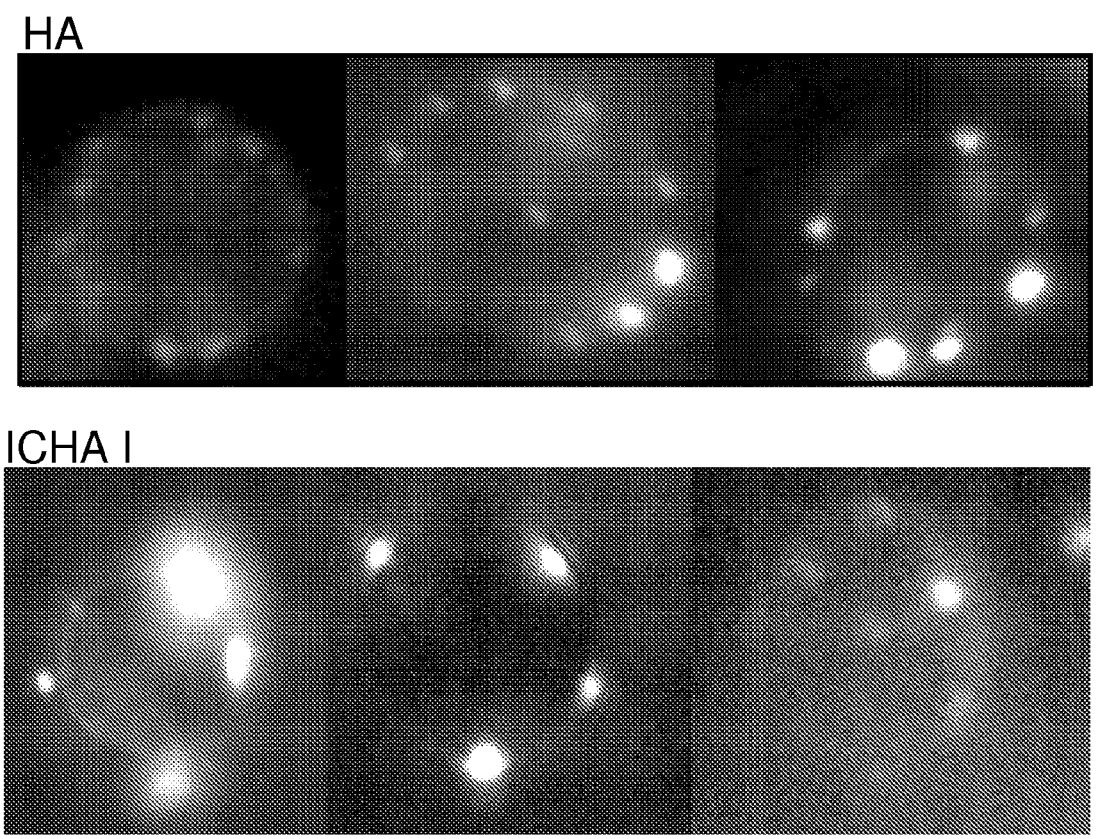
FIG. 6 shows binding of HA and ICHA I to rabbit erythrocytes.
Figure 7:
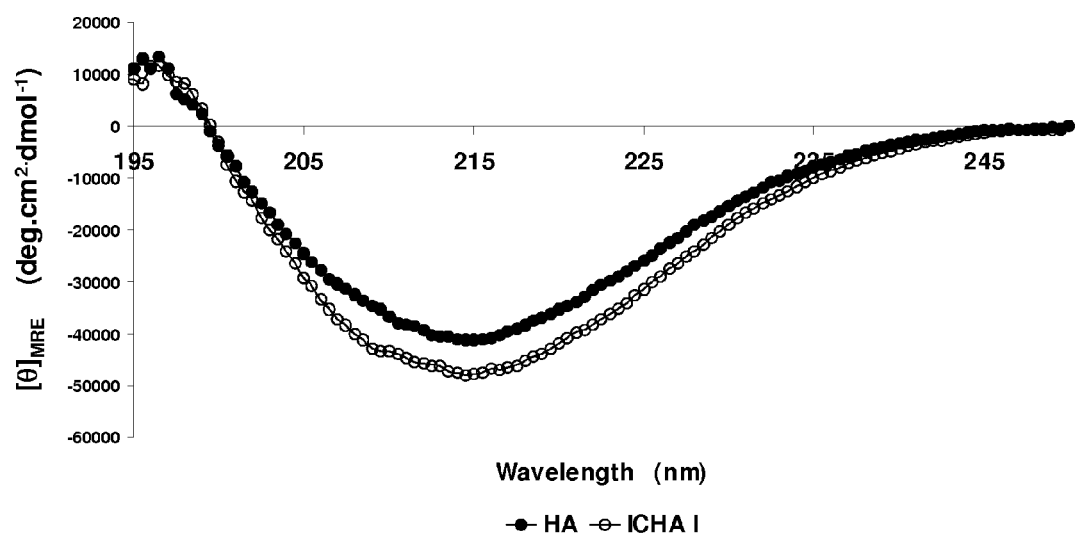
FIG. 7 shows far UV circular dichroism spectra performed over a wave-length range of 190-250 nm.
Figure 8:
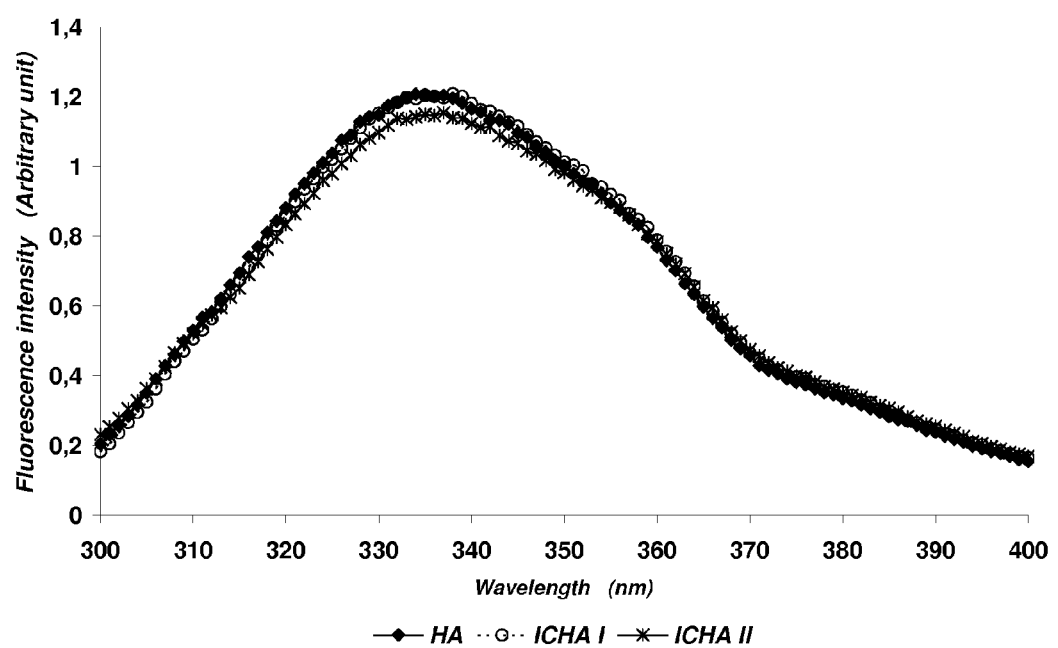
FIG. 8 shows intrinsic fluorescence of HA, ICHA I and ICHA II, using an excitation wavelength of 280 nm and the emission spectra were recorded from 300 to 400 nm.
Figure 13:
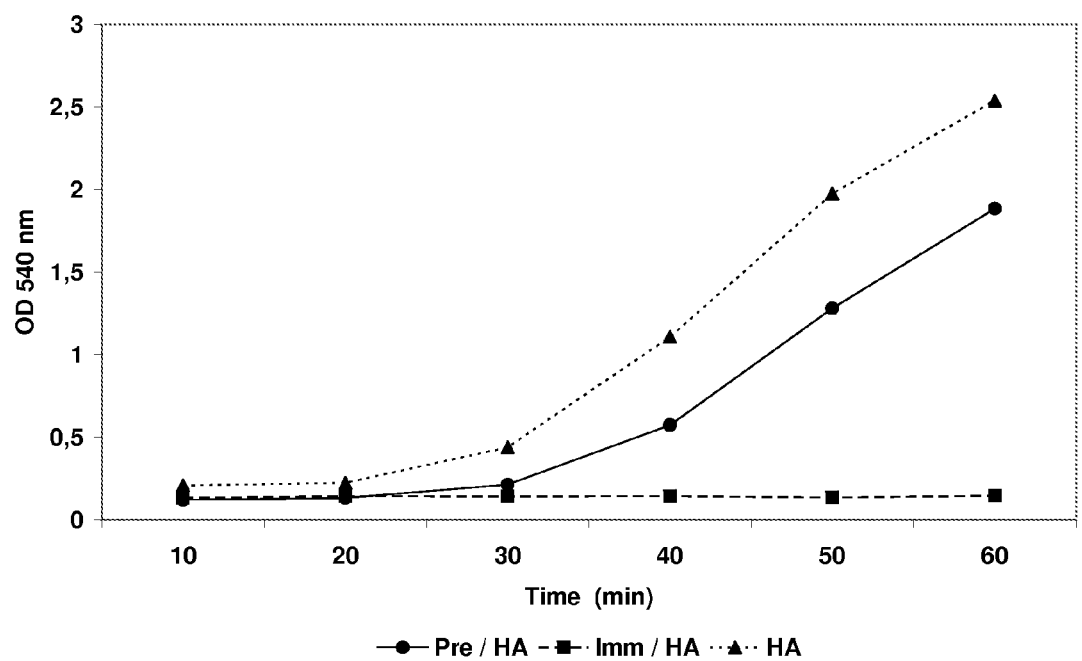

FIG. 13 shows the results in respect to the immunization of rabbit with ICHA I 003 induce neutralizing antibodies against HA. Pre and Imm correspond to the preimmune serum and the serum obtained after 3 injections, respectively. Haemolysis assays have been performed according to the procedure described in FIG. 4.

Figure 14:
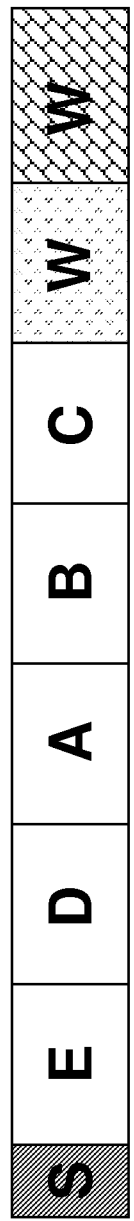

FIG. 14 shows the structural organization of the Staphylococcal protein A. "S" represents the signal sequence; "W" represents the wall-spanning region; "Wr" is composed of an octapeptide repeat, and "Wc" is a non-repeated region. "A, B, C, D, E" represent extracellular regions.

Figure 15:
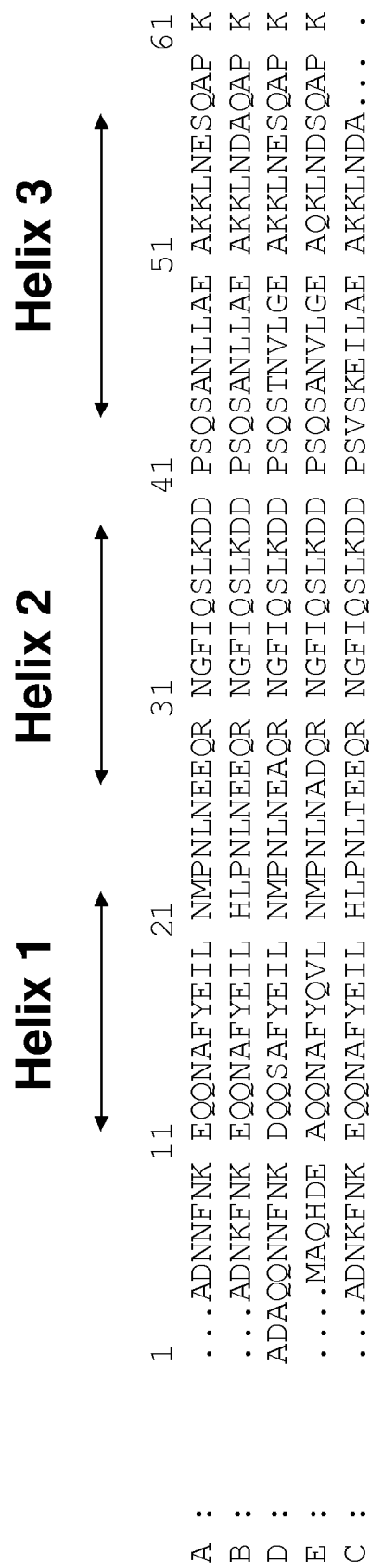

FIG. 15 shows the alignment of the amino acid sequences of the five naturally occurring Staphylococcal protein A domains. The three a helices are delimited by arrows. The sequences A, B, D, E, and C correspond to SEQ ID NOS: 74, 79, 76, 77, and 78, respectively.

Figure 16:
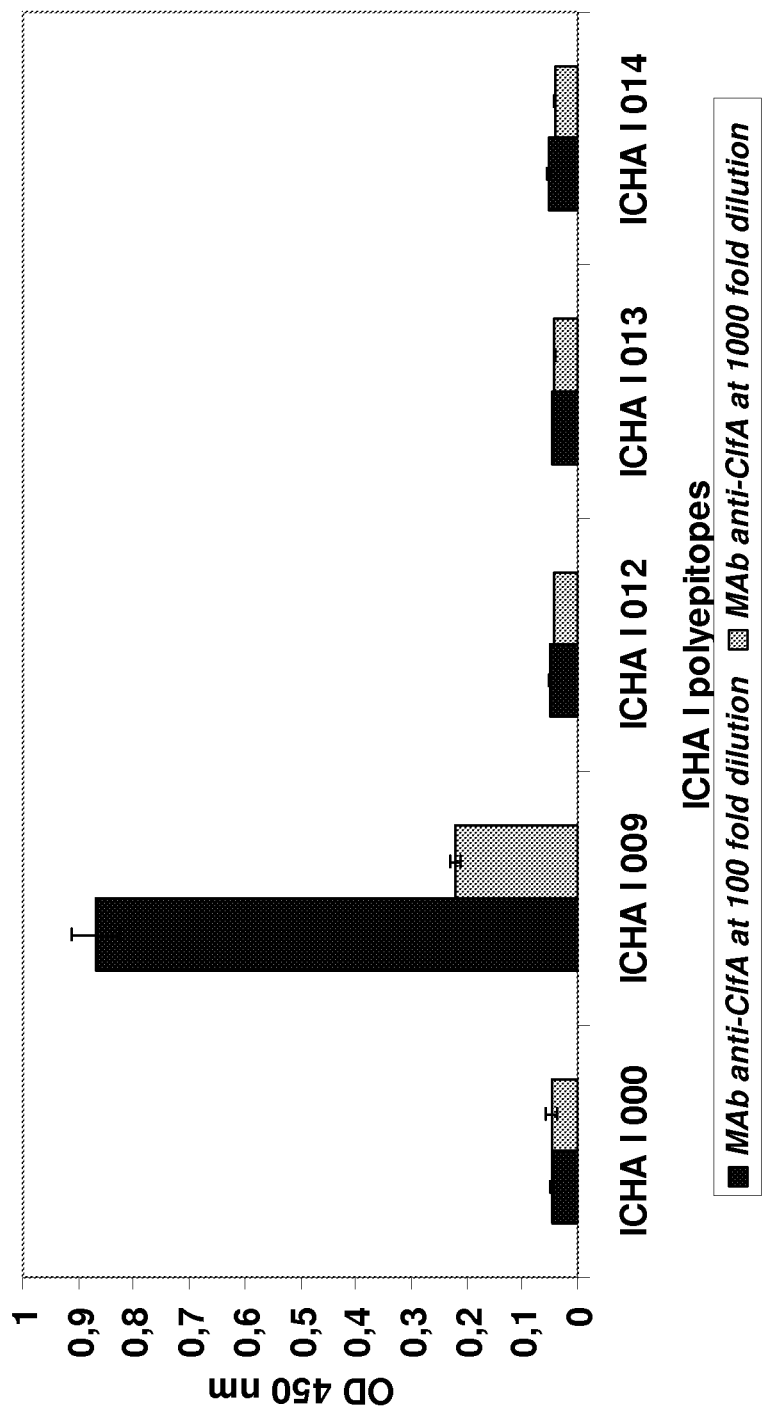

FIG. 16 shows the ELISA reactivity of the SpA (*Staphylococcus* protein A) derivatives ICHA polytopes to mouse anti-Clfa monoclonal antibody. The full immunoglobulin-binding domain (ICHA I 009) and the three α-helices of the SpA domain were coated into microtitre ELISA plates. The protein ICHA I 000 was taken as control. The five polyepitopes were tested for the recognition of mouse IgG antibody in ELISA experiments. The bound antibodies were detected with horseradish peroxidase (HRP)-labelled goat anti-mouse IgG. The reaction was developed using TMB substrate during 10 minutes, the enzyme reaction was stopped by addition of 1M H2SO4 and the absorbance was read at 450 nm.

The present invention will be described further by the following examples which are not to be understood to limit the scope of the present invention in any way.

EXAMPLES

Example 1

Construction of Inactivated Carrier Hemolysin alpha (ICHA I and ICHA II)

Figure 1:
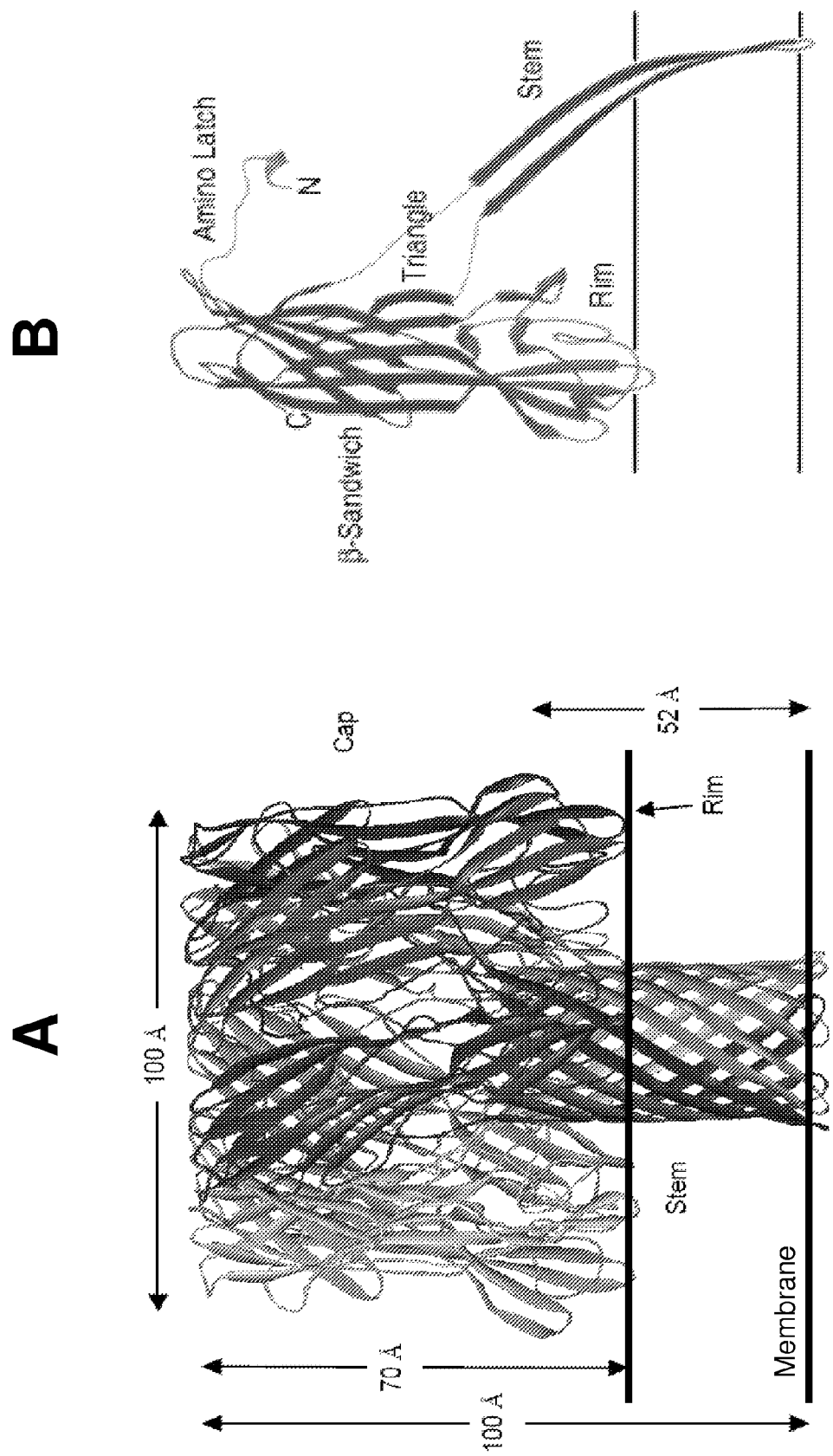
Figure 1:
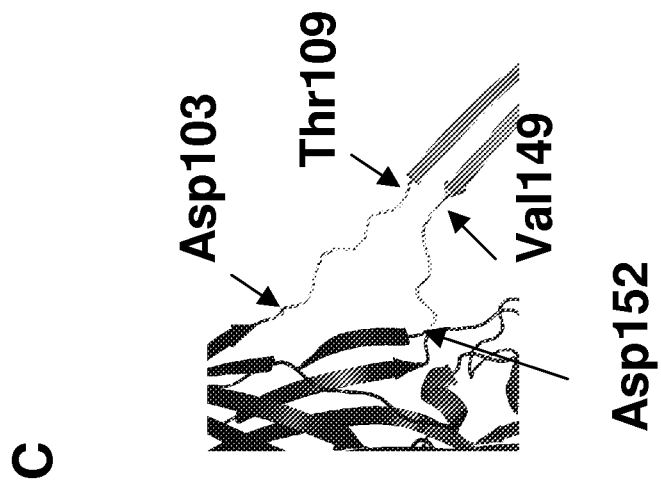
Figure 2:
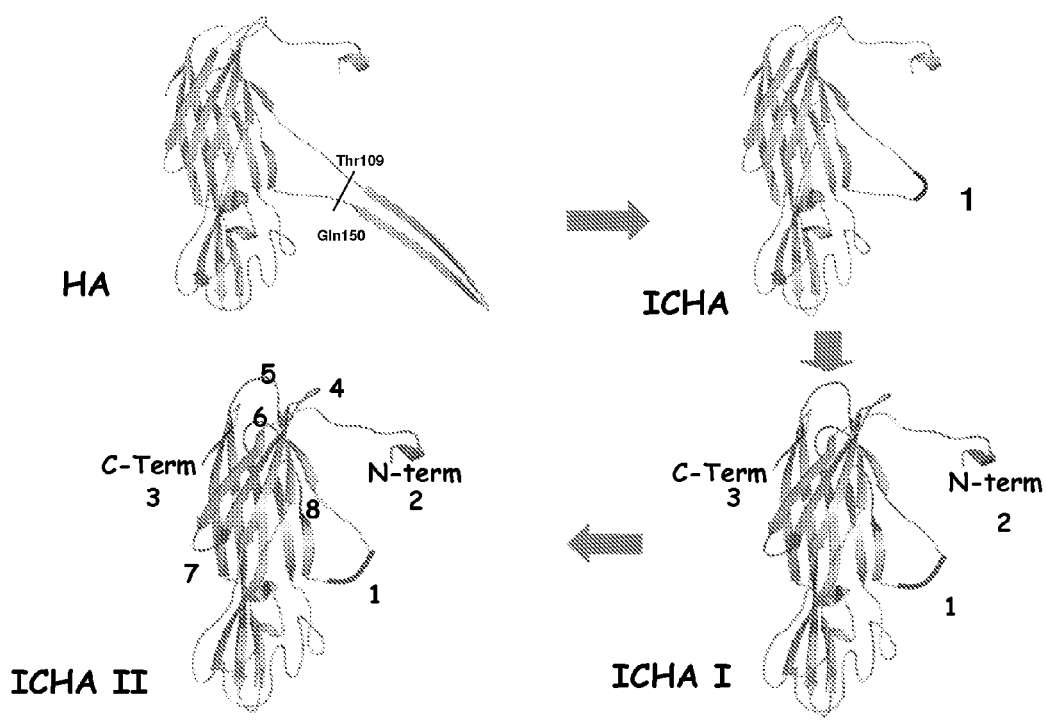

The inactivated carrier hemolysin alpha (HA) (ICHA I and ICHA II) according to the present invention was constructed as follows: The inactivation of hemolysin alpha (HA) toxicity was performed by the substitution of 42 amino acids of the central domain encompassing the residues Thr109 to Gln150 with the tripeptide Pro-Gly-Asn (FIG. 2, table 1). This peptide permits the creation of a SmaI restriction site in the corresponding nucleotide sequence, which allows the subsequent internal cloning of large heterologous nucleotidic sequences into the ICHA encoding gene. The substituted fragment corresponds to the stem domain of HA (FIGS. 1 and 2). This domain is flanked at its N- and C-terminal extremities by the triangle region. The stem domain is characterized by the two anti-parallel β-strands of the central glycine-rich domain and participates to the formation of the channel wall by self-assembling in a 14 strand β-barrel.

The challenge of this step consisted of both, to develop a toxin that loses its haemolytic activity and to create a permissive insertion site of large heterologous polypeptides without interfering with the other biological properties of the carrier. These ones are structure related characteristics of the native protein, the capacity to bind lipidic bilayers and to form oligomer, and the ability to induce neutralizing antibodies of the HA haemolytic activity. To maintain these conditions, the stem domain was substituted while the integrity of the triangle region essentially was maintained. This region is used as a natural linker to avoid steric hindrance between the insert and the carrier.

The insertion of additional restriction sites into the gene encoding ICHA gives rise to ICHA I and ICHA II. These restriction sites offer the possibility to display small polypeptides at the surface of the carrier protein. In regard to the 3D structure of HA, no insertion site was created in the rim domain of HA in order to avoid structural modification and thus its immunogenicity. High resolution crystallographic studies of HA-phospholipid complexes define the interaction region in a crevice between the rim and the stem domains. Consequently, seroneutralization of HA could be obtained by prevention of the interaction of the HA monomer to cell membrane by way of the binding of antibodies to the rim domain. All the modifications introduced into HA are listed in Table 1.

The engineered genes coding for ICHA I and ICHA II were cloned into pET28b to give pET28b ICHA I and pET28b ICHA II. For each of these constructions, it was possible to express the protein in fusion with a polyhistidine tag at its C-terminal extremity. The amino acid sequences of alpha hemolysin and its related mutated forms ICHA I and ICHA II are described in the sequence listings. SEQ ID NO: 1 refers to the wild-type alpha hemolysin of Staphylococcus aureus, whereas SEQ ID NO: 3 and SEQ ID NO: 5 refer to the constructs ICHA I and ICHA II, which are modified according to the details given in table 1.

Plasmid Construction

Hemolysin Alpha:

The alpha-HL gene was obtained by PCR amplification of the genomic DNA of S. aureus strain using the NcoIHL primer and the H3HLHis primer (table 4). The NcoIHL primer creates a new initiation codon and an NcoI site immediately before the Ala codon of the mature polypeptide. The H3HLHis creates a new HindIII site in the 3' end.

The 26 amino acid hydrophobic leader sequence was deleted. The PCR amplified fragment was directly inserted into the pGEM vector. The alpha-HL coding gene was completely sequenced and recloned between the NcoI and HindIII sites of the pET28b(+) expression vector.

ICHA:

DNA encoding central residues Thr109-Gln150 was removed from the HA gene by the overlap extension PCR method. In separate PCRs, two fragments of the target gene were amplified. The first reaction used the flanking NcoIHL primer which hybridized upstream from the hemolysin alpha encoding gene and the internal antisense HL108-primer which hybridized with the site of deletion. The second reaction used the flanking antisense H3HLHis primer which hybridized downstream of the hemolysin alpha encoding gene and the internal sense HL108+ primer which hybridized with the site of deletion. The two fragments were purified by agarose gel electrophoresis and fused by denaturating and annealing them in a subsequent primer extension reaction. By addition of extra flanking primers, the 778 by fragment was further amplified by PCR, purified and cloned into pGEM vector. The ICHA gene was sequenced in its entirety. No sequence differences from the HL gene were observed except for the deleted residues (Thr109-Gln150), which were replaced by Pro-Gly-Asn in the ICHA gene. The ICHA coding gene was recloned between the NcoI and HindIII sites of the pET28b(+) expression vector.

ICHA II:

The overlap extension PCR method was used to introduce a new restriction endonuclease sites onto the ICHA coding gene. In separate PCRs, two fragments of the target gene were amplified. The first reaction used the flanking NcoIHL primer and the internal restriction endonuclease site-reverse primer which hybridized with the site of insertion. The second reaction used the flanking H3HLHis primer and the internal restriction endonuclease site-reverse-sense primer which hybridized with the site of insertion. The two fragments were purified by agarose gel electrophoresis and fused by denaturating and annealing them in a subsequent primer extention reaction. By addition of extra flanking primers, the ICHA I plus the new restriction site fragment was further amplified by PCR, purified and cloned into pGEM vector. The ICHA I plus the new restriction site coding gene was completely sequenced and used as matrix to introduce a second new restriction endonuclease site onto the ICHA coding gene. This strategy has been used to create the restriction endonuclease sites for BamHI, PstI, SacI, EcoRI and NheI.

TABLE 1

Modifications introduced into alpha-hemolysin. The table shows the amino acid sequence region where amino acids have been added. Amino acid residues inserted are shown in bold. In site No: 1 the underlined amino acids are the tripeptide Pro-Gly-Asn that substitutes the 42 amino acids at position 109 to 150 of the central domain of the wild-type sequence.

| restriction site (insertion site No:) | region of alpha-hemolysin amino acid sequence* | SEQ ID NO: | ICHA-I amino acid sequence | ICHA II amino acid sequence | SEQ ID NO: |
|---|---|---|---|---|---|
| NcoI (site No: 2) | 1 ADSDI 5 | SEQ ID NO: 19 | MADSDI | MADSDI | SEQ ID NO: 20 |
| BamHI (site No: 7) | 30 KENGMH 35 | SEQ ID NO: 21 | | KENGSGMH | SEQ ID NO: 22 |
| PstI (site No: 4) | 43 IDDKHN 48 | SEQ ID NO: 23 | | IDDLQKNH | SEQ ID NO: 24 |
| SacI (site No: 6) | 92 DNEVAQ 97 | SEQ ID NO: 25 | | DNEELVAQ | SEQ ID NO: 26 |
| SmaI (site No: 1) | 106 SID 108 -151 PDF 153 | | SIDPGNPDF | SIDPGNPDF | SEQ ID NO: 27 |

TABLE 1-continued

Modifications introduced into alpha-hemolysin. The table shows the amino acid sequence region where amino acids have been added. Amino acid residues inserted are shown in bold. In site No: 1 the underlined amino acids are the tripeptide Pro-Gly-Asn that substitutes the 42 amino acids at position 109 to 150 of the central domain of the wild-type sequence.

| restriction site (insertion site No:) | region of alpha-hemolysin amino acid sequence* | SEQ ID NO: | ICHA-I amino acid sequence | ICHA II amino acid sequence | SEQ ID NO: |
|---|---|---|---|---|---|
| EcoRI (site No: 8) | 155 TILESP 160 | SEQ ID NO 28 | | TILEFESP | SEQ ID NO: 29 |
| NheI (site No: 5) | 235 DRKASK 240 | SEQ ID NO: 30 | | DRKASASK | SEQ ID NO: 31 |
| HindIII (site No: 3) | 288 KEEMTN 293 | SEQ ID NO: 32 | KEEMTNKL | KEEMTNKL | SEQ ID NO: 33 |

*numbers indicate amino acid positions in respect to SEQ ID NO: 1

Example 2

Engineering of Polyepitopes Related to ICHA I

All the heterologous epitopes displayed into ICHA I are listed in table 2. The resulting polyepitopes are listed and described in table 3.

TABLE 2

Epitopes and amino acid sequences used as homologous sequence for integration in the recombinant alpha hemolysin polypeptide.

| virulence factor | entry name and accession number | amino acid fragment | localization on the virulence factor (amino acid positions) | insertion site in ICHA I No: |
|---|---|---|---|---|
| SEB | P01552 | SEQ ID NO: 7 | 179-188 | 2 |
| SEB | ETXB_STAAU | SEQ ID NO: 8 | 176-191 | 3 |
| TSST-1 | P06886 TSST_STAUU | SEQ ID NO: 9 | 87-101 | 3 |
| PBP2a | P07944 PBP_STAUU | SEQ ID NO: 10 | 376-451 | 1 |
| BlaZ | P00807 BLAC_STAUU | SEQ ID NO: 11 | 134-190 | 1 |
| FnBP | Q8NUU7 FNBA_STAAW | SEQ ID NO: 12 | 764-780 802-818 | 1 + 3 |
| FnBP | | SEQ ID NO: 13 | 842-855 | 1 + 3 |
| ClfA | Q6GIK4 CLFA_STAAR | SEQ ID NO: 14 | 501-559 | 1 |
| Protein A | A1KDX6_STAUU | SEQ ID NO: 15 | 187-248 | 1 |
| Protein A | | SEQ ID NO: 16 | 187-205 | 1 |
| Protein A | | SEQ ID NO: 17 | 206-223 | 1 |
| Protein A | | SEQ ID NO: 18 | 224-248 | 1 |

TABLE 3

The series of ICHA polyepitopes constructed in the present invention.

| construct | insertion site No: 1 | insertion site No: 2 | insertion site No: 3 |
|---|---|---|---|
| ICHA I 000 | | | |
| ICHA I 001 | | SEB (179-188) | |
| ICHA I 002 | | | TSST (87-101) |
| ICHA I 003 | | SEB (179-188) | TSST (87-101) |
| ICHA I 004 | | | SEB (176-191) |
| ICHA I 005 | PBP2a (376-451) | | |
| ICHA I 006 | BlaZ (134-190) | | |
| ICHA I 007 | FnBP (764-780/ 842-855) | | |
| ICHA I 008 | ClfA (501-559) | | |
| ICHA I 009 | Protein A (187-248) | | |
| ICHA I 010 | ClfA (501-559) | | FnBP (764-780/ 842-855) |
| ICHA I 011 | ClfA (501-559) | | SEB (176-191)/ TSST (87-101) |
| ICHA I 012 | Protein A (187-205) helix 1 | | |
| ICHA I 013 | Protein A (206-223) helix 2 | | |
| ICHA I 014 | Protein A (224-248) Helix 3 | | |

The Recombinant ICHA I Polypeptide Wherein the Heterologous Sequence is Inserted to the site 1.

The heterologous sequence was amplified by PCR from the genomic DNA of *S. aureus* using specific oligonucleotide primers (table 4). The DNA amplification was performed using pfx DNA polymerase; the PCR product was cloned into a SmaI site into pET28b-ICHA vector to produce the recombinant peptide.

The Recombinant ICHA I Polypeptide Wherein the Heterologous Sequence is Fused to the Site 2 or 3.

The large heterologous sequence was amplified by PCR from the genomic DNA of *S. aureus* using specific oligonucleotide primers. The primers used create the flanking NcoI or HindIII sites. The DNA amplification was performed using pfx DNA polymerase; the PCR product was cloned into an NcoI or HindIII site into pET28b-ICHA vector to produce the recombinant peptide.

The small heterologous sequence was amplified by hybridation of two complementary oligonucleotide primers. The oligonucleotide primers used create a new NcoI or HindIII restrictions site flanking the heterologous sequence. The hybridation product was cloned into an NcoI or HindIII site into pET28b-ICHA vector to produce the recombinant peptide.

TABLE 4

| Synthetic oligonucleotide primers for constructing the constructs | | | SEQ ID NO: |
|---|---|---|---|
| Primer | Used technique | Sequence (5'-3')[a] | |
| NcoIHL | PCR | GGCCATGGCAGATTCTGATATTAATATTAAAACCGGTACTACAGAT | SEQ ID NO: 34 |
| H3HLHis | PCR | GCAAGCTTATTTGTCATTTCTTCTTTTTCCCAATCGATTTTATA | SEQ ID NO: 35 |
| HL108+ | PCR | GATCCCGGGAACCCTGATTTCAAAACAATTTTAGAGAGCCCA | SEQ ID NO: 36 |
| HL108- | PCR | AATTGTTTTGAAATCAGGGTTCCCGGGATCAATCGAATTTCTTGGATAGTAATCAGATAT TTG | SEQ ID NO: 37 |
| BamHI_sens | PCR | TATGATAAAGAAAATGGATCCGGCATGCACAAAAAA | SEQ ID NO: 38 |
| BamHI_reverse | PCR | TTTTTTGTGCATGCCGGATCCATTTTCTTTATCATA | SEQ ID NO: 39 |
| PstI_sens | PCR | AGTTTTATCGATGATCTGCAGAAAAATCATAATAAA | SEQ ID NO: 40 |
| PstI_reverse | PCR | TTTATTATGATTTTTCTGCAGATCATCGATAAAACT | SEQ ID NO: 41 |
| EcoRI_sens | PCR | TTCAAAACAATTTTAGAATTCGAGAGCCCAACTGAT | SEQ ID NO: 42 |
| EcoRI_reverse | PCR | ATCAGTTGGGCTCTCGAATTCTAAAATTGTTTTGAA | SEQ ID NO: 43 |
| NheI_sens | PCR | ACTATGGATAGAAAAGCTAGCGCATCCAAACAACAA | SEQ ID NO: 44 |
| NheI_reverse | PCR | TTGTTGTTTGGATGCGCTAGCTTTTCTATCCATAGT | SEQ ID NO: 45 |
| SacI_sens | PCR | TTGCACTGGACTTCAGAGCTCACAAATTGGAAAGGT | SEQ ID NO: 46 |
| SacI_reverse | PCR | ACCTTTCCAATTTGTGAGCTCTGAAGTCCAGTGCAA | SEQ ID NO: 47 |
| SEB sens | Hybridization | CCATGGGCAAAAAGAAAGTGACAGCGCAGGAGCTTGACGCCATGG | SEQ ID NO: 48 |
| SEB reverse | Hybridization | CCATGGCGTCAAGCTCCTGCGCTGTCACTTTCTTTTTGCCCATGG | SEQ ID NO: 59 |
| SEB large sens | Hybridization | AAGCTTCAAACTAATAAGAAAAAGGTGACTGCTCAAGAATTAGATTACCTAACTAAGCTT | SEQ ID NO: 54 |
| SEB large reverse | Hybridization | AAGCTTAGTTAGGTAATCTAATTCTTGAGCAGTCACCTTTTTCTTATTAGTTTGAAGCTT | SEQ ID NO: 55 |
| TSST-1 sens | Hybridization | AAGCTTTTTCCGAGTCCTTATTATAGCCCTGCTTTTACAAAAGGGGAAAAGCTT | SEQ ID NO: 50 |
| TSST-1 reverse | Hybridization | AAGCTTTTCCCCTTTTGTAAAAGCAGGGCTATAATAAGGACTCGGAAAAAGCTT | SEQ ID NO: 51 |
| SEB-TSST sens | Hybridization | AAGCTTCAAACTAATAAGAAAAAGGTGACTGCTCAAGAATTAGATTACCTAACTGGGAG CGGGTTTCCGAGTCCTTATTATAGCCCTGCTTTTACAAAAGGGGAAAAGCTT | SEQ ID NO: 70 |
| SEB-TSST reverse | Hybridization | AAGCTTTTCCCCTTTTGTAAAAGCAGGGCTATAATAAGGACTCGGAAACCCGCTCCCAG TTAGGTAATCTAATTCTTGAGCAGTCACCTTTTTCTTATTAGTTTGAAGCTT | SEQ ID NO: 71 |
| CIfA sens | PCR | TTTCTTGGTGATTTAGCACTACGTTCGACATTTTAT | SEQ ID NO: 52 |
| CIfA reverse | PCR | TGGTAGCTCTGGAATGGGTTCAATTTCACCAGGCTC | SEQ ID NO: 53 |
| FnBP sens | Hybridization | TGGTCGAAATATGAACAAGGTGGCAATATTGTAGATATCGATTTCGACAGTGTACCTCA ATTCGGTGGACACAATAGTGTTGACTTTGAAGATACACGTCAA | SEQ ID NO: 56 |

TABLE 4-continued

Synthetic oligonucleotide primers for constructing the constructs

| Primer | Used technique | Sequence (5'-3')[a] | SEQ ID NO: |
|---|---|---|---|
| FnBP reverse | Hybridization | TTGACGTGTATCTTCAAAGTCAACACTATTGTGTCCACCGAATTGAGGTACACTGTCGA AATCGATATCTACAATATTGCCACCTTGTTCATATTTCGACCA | SEQ ID NO: 57 |
| FnBP-HindIII sens | PCR | <u>AAGCTT</u>AAATATGAACAAGGTGGCAATATTGTAGAT | SEQ ID NO: 72 |
| FnBP-HindIII reverse | PCR | <u>AAGCTT</u>TGTATCTTCAAAGTCAACACTATTGTGTCC | SEQ ID NO: 73 |
| MecA sens | PCR | TGTGCGGGCATGAGTAACGAAGAATATAATAAATTA | SEQ ID NO: 58 |
| MecA reverse | PCR | CCCACATACCACTTCATAGCGTGTAACGTTGTAACC | SEQ ID NO: 59 |
| BlaZ sens | PCR | GGTGGAATCAAAAAAGTTAAACAACGTCTAAAAGAA | SEQ ID NO: 60 |
| BlaZ reverse | PCR | TAATTTTCCATTGGCGATAAGTTTATTAAGGGTCTTACC | SEQ ID NO: 61 |
| Protein A sens | PCR | AACAATTTCAACAAAGAACAACAAAATGCTTTCTAT | SEQ ID NO: 62 |
| Protein A reverse | PCR | TTTTTTGTTGTCTTCCTCTTTTGGTGCTTGAGCATC | SEQ ID NO: 63 |
| Protein A-H1 sens | PCR | AACAATTTCAACAAAGAACAACAAAATGCTTTCTAT | SEQ ID NO: 64 |
| Protein A-H1 reverse | PCR | GTTAGGTAAATGTAAAGTTTCATAGAAAGC | SEQ ID NO: 65 |
| Protein A-H2 sens | PCR | TAACTGAAGAACAACGTAACGGCTTCATCC | SEQ ID NO: 66 |
| Protein A-H2 reverse | PCR | TGATGGATCGTCTTTAGGGCTTTGGATGAA | SEQ ID NO: 67 |
| ProteinA-H3 sens | PCR | GTGAGCAAAGAAATTTTAGCAGAAGCTAAA | SEQ ID NO: 68 |
| ProteinA-H3 reverse | PCR | TTTTTTGTTGTCTTCCTCTTTTGGTGCTTGAGCATC | SEQ ID NO: 69 |

[a]Restriction sites are underlined.

Example 3

Production, Purification and Renaturation of HA, ICHA I, ICHA II and ICHA Polyepitopes

[00181] The procedure employed to deliver purified and refolded protein depends of the presence of a polyhistidine tag at the C-terminal extremity of the protein.

Production

The recombinant HA protein and its derivatives were overproduced in *E. coli* BL21(DE3) harbouring the desired pET28b plasmid. Ten milliliter culture of LB containing 50 μg/ml kanamycin was initiated from a single colony of freshly transformed plate and grown overnight at 37° C. One liter of TB medium containing 50 μg/ml kanamycin was inoculated and allowed to grow at 37° C. When the OD600 nm reached a value of 1.2, IPTG was added at a final concentration of 1 mM and the culture was allowed to grow for an additional 4 h at 37° C. At this temperature, the protein is mainly produced in the form of inclusion bodies. Soluble protein expression can be obtained when inducing at 18° C.

Purification and Renaturation of His-Tagged Proteins

Figure 3:
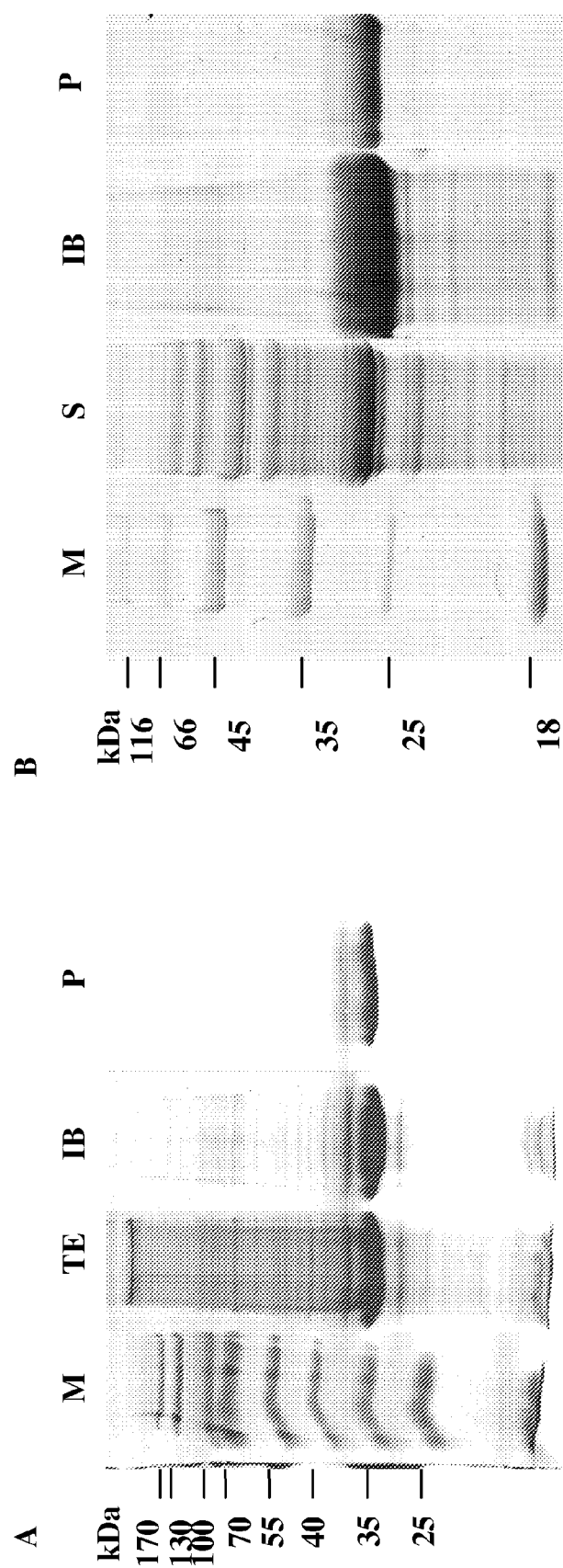

The bacteria were pelleted at 3000×g for 15 minutes at 4° C. It was found that most of the protein existed in the form of inclusion bodies. The cells were resuspended in buffer A (50 mM Tris-HC1, pH 8.0, 1 mM EDTA, 100 mM NaC1) and were lysed by mild sonication. The insoluble protein fraction was recovered by centrifugation at 12,000×g for 30 min at 4° C. and resuspended in buffer B (50 mM Tris-HC1, pH 8.0, containing 0.5% (v/v) TRITON® X-100) and allowed to shake for 16 h at 4° C. The inclusion bodies were successively recovered by centrifugation at 30,000×g for 30 minutes at 4° C., resuspended in buffer C (50 mM Tris-HC1, pH 8.0, 8 M urea) and incubated at 4° C. for 16 h, with shaking. The inclusion bodies were then centrifuged 30,000×g for 30 minutes, and the supernatant was loaded onto a metal chelate affinity column (NiNTA agarose) equilibrated in buffer C. The proteins were eluted with a linear gradient of 500 mM imidazol in buffer C. Fractions were collected and analyzed by SDS-PAGE. Peak fractions were pooled and diluted in tenfold phosphate buffer saline (PBS) containing 0.5% N-Lauroyl-sarcosine. The protein was renatured by dialysis against PBS buffer and concentrated by ultrafiltration with an Amicon PM-10 membrane. FIG. 3 illustrates the purification of the recombinant HA and the recovery of its haemolytic activity after the renaturation step, respectively.

Purification and Renaturation of Non-His-Tagged Proteins

The inclusion bodies were prepared as described above for His-tagged proteins and resuspended in buffer D (50 mM Tris-HC1, pH 8.5, 8 M urea) and incubated at 4° C. for 16 h, with shaking. The inclusion bodies were then centrifuged 30,000×g for 30 minutes, and the supernatant was subjected to anion-exchange chromatography on Source 15Q (GE Healthcare) column previously equilibrated with five column volumes of buffer D. After washing the column with five column volumes of equilibration buffer, the bound proteins were eluted at a flow rate of 3 ml/min with a linear gradient of 500 mM NaCl in buffer D over 10 column volumes. Fractions were collected and purity was assessed by SDS-PAGE as greater than 98%. Peak fractions were pooled and diluted in tenfold phosphate buffer saline (PBS) containing 0.5% N-Lauroyl-sarcosine. The protein was renatured as described above for His-tagged proteins.

Example 4

Absence of Haemolytic Activity with ICHA I and ICHA II

The purified proteins HA, ICHA I and ICHA II were assayed at a final concentration of 0.3 mg/ml for haemolytic activity against washed defibrinated rabbit erythrocytes (rRBC) diluted 1/20 in PBS. These erythrocytes are hypersensitive to HA. In comparison, a 400-fold-higher concentration of the toxin is required to lyse human erythrocytes. After 30 minutes of incubation at 30° C., the rRBC are pelleted by centrifugation and the haemolysis is monitored by measuring haemoglobin in the supernatant at 540 nm. The FIG. 4 attests of the absence of haemolytic activity when using large quantities of ICHA I and ICHA II. In addition, a comparative analysis with a commercial HA purified from S. aureus supernatant, indicates that the refolding of HA according to our process is efficient.

Example 5

ICHA I, ICHA II and ICHA Polyepitopes Bind to Lipidic Bilayer, Form Oligomer and Conserve Spectroscopic Features of HA Analysis by Western Blotting 40 μg of proteins (HA, ICHA I and ICHA I 008) was incubated at 37° C. during 15 minutes with 300 μl of a 1:20 red blood cells dilution. Membrane fraction was then isolated by 30 minutes centrifugation at 13,000 g. The pellet was resuspended in 300 μl cold water and denaturating solution (0.06 M Tris-HCl, pH 6.8, 1% SDS, 9.5% glycerol, 3.3% mercaptoethanol, 0.002% bromophenol blue) was added. Samples were loaded on a SDS 10%-PAGE. Binding and oligomer formation were examined by Western blotting using a monoclonal anti-HA antibody and a monoclonal anti-IgG mouse conjugated to HRP (Amersham Pharmacia). Each loaded sample corresponded to 1.8 μg of protein. The results are presented in FIG. 5. As a conclusion, it is demonstrated that ICHA I and its related polyepitopes are still able to bind to lipidic bilayer and to form oligomer in a similar way that HA.

Analysis by Direct Fluorescence

HA and ICHA I proteins were labeled with the AMCA-X fluorophore (AnaTag™ AMCA-X Protein Labeling kit, ANASpec), excitation at 347 nm and emission at 447 nm. Erythrocytes were then incubated for 10 minutes at 25° C. with 40 μg of HA-AMCA-X or ICHA I-AMCA-X. Cells were washed twice with PBS and then were photographed with a cooled AxioCam MRm (Zeiss) mounted on an Zeiss Axio Imager.Z1 microscope through an EC Plan-NEOFLUAR 100×1.3 oil immersion objective in fluorescence (with a filter set 20 (Zeiss)). Images were taken using the AxioVision Rel 4.5 (Zeiss). The results are presented in FIG. 6. These data confirm that ICHA I is still able to bind to the lipidic bilayer and to form protein rafts at the surface of cell membranes.

Analysis by Fluorescence and Far UV-CD

Circular Dichroism (CD)

In order to evaluate the secondary structure changes induced by site insertion on the HA protein, far UV circular dichroism spectra were measured from 190-250 nm using a JASCO J-810 spectropolarimeter. The scanning speed was 50 nm/minute. Ten scans per sample were performed and the protein concentrations were 4.2 μM in PBS buffer for the two proteins. The mean residue ellipticity, [θ], is given in deg. $cm^2.dmol^{-1}$: $[\theta]=[\theta]_{obs}$ (MRW/10 Ic), where $[\theta]_{obs}$ is the ellipticity measured in millidegrees, MRW, is the mean residue molecular weight of the protein, c is the concentration of the sample in mg/ml, and I is the optical path length of the cell in cm.

The CD spectra indicate that the ICHA I protein possesses a high β-sheet content and are similar to CD spectra of alpha-hemolysin (FIG. 7).

Fluorescence Spectroscopy

Structural changes induced by the insertion sites on the HA protein were examined by intrinsic fluorescence using an excitation wavelength of 280 nm and the emission spectra for 1.5 μM HA, ICHA I and ICHA II were recorded from 300 to 400 nm. All spectra were recorded at protein concentrations of 4.2 μM in PBS buffer. Fluorescent measurements were performed on AMINCO SLM 8100 spectrofluorometer.

Both fluorescence spectroscopy and far UV CD spectra for the HA derivatives are highly similar to those of the HA protein, indicating that the ICHA I and ICHA II obtained retains its native conformation (FIG. 8).

Example 6

ICHA Polyepitopes Immunopotentiate Antibodies Against the Inserts and HA in a Murine Model Immunization and Antibody Response Against ICHA I 008 and Clfa Fragment.

A 177 by Clfa fragment, corresponding to amino acid Gly501 to Glu559 of the wild-type Clfa, was amplified by PCR from the pET28b-ICHA-Clfa plasmid using primers that incorporated sequences for restriction endonucleases NcoI site at the 3' and HindIII site at the 5' ends. The amplified fragments were double digested with NcoI and HindIII and ligated into the same sites of the pET28b vector to produce the recombinant peptide. His-tagged Clfa fragment was purified by affinity chromatography using metal chelate affinity column (NiNTA agarose).

Female BALb/c mice, 8 to 10 weeks old, were purchased from Harlan (Horst, The Netherlands). Three groups of ten mice were immunized subcutaneously with 1.33 nmoles of ICHA I 008 (50 μg) or Clfa fragment (10.8 μg) or ICHA I (40 μg) emulsified in Quil A adjuvant. Immunizations were done two times giving three weeks interval between immunizations. One more mice group was immunized with the same volume of Quil A adjuvant in PBS and was taken as control. Sera were collected on days 0, 35 and 52 (indicated in the figure legend as j0, j35 and j52 respectively) by tail bleeding and stored at −20° C. until use. Specific antibodies responses were screened by ELISA for reactivity with MBP-Clfa fusion protein as coating antigen.

Sera collected at each time point from individual mice (test and control groups) were tested for the recognition of C1fA fragment by ELISA. Microtitre ELISA plates (Nunc-Immuno Plate, Roskilde, Denmark) were coated with MBP-ClfA (250 ng/well) in coating buffer (0.05 M carbonate-bicarbonate buffer, pH 9.6) and incubated during one hour at 20° C. The plates were washed three times with phosphate buffered saline containing 0.05% TWEEN 20®(PBST) and blocked with 150 μl of 3% casein hydrolysate in PBS for 1 h at 20° C. Test sera serially diluted two fold in PBST starting with 1:50 were incubated in wells (50 μl/well) for 1 h at 20° C. The wells were washed three times with PBST. The bound antibodies were detected by 30 minutes incubation at 20° C. with horseradish peroxidase (HRP)-labelled goat anti-mouse IgG. The reaction was developed using tetramethylbenzidine (TMB) during 10 minutes, the enzyme reaction was stopped by addition of 1M $H_2SO_4$ and the absorbance was read at 450 nm.

The analysis of total IgG levels (FIG. 9a) shows that the immunizations with Clfa fragment displayed into ICHA I 008 induce the stronger serum anti-Clfa responses compared to immunizations with Clfa alone, suggesting that the carrier protein elicit the immune response against this polypeptide.

Sera from immunized mice were compared for anti-Clfa antibodies by ELISA at a serum dilution 1:800 as a function of time (in days) (see FIG. 9b). In the case of ICHA I 008, high titers of anti-Clfa are induced and a maximum is reached at day 35 indicating that the second immunization is not require to obtain this maximum. For immunizations with the Clfa fragment alone, the monitoring of anti-Clfa antibodies indicates that a second immunization was required to increase the immune response against Clfa and that no plateau was detected at day 52. These results suggest that the carrier protein elicit the immune response against this polypeptide.

FIG. 9c indicates that all the animals elicited antibodies against Clfa when they received ICHA I 008. The low variability observed for the humoral responses indicated that the ten mice of these group had a similar response to the Clfa fragment. In the case of immunizations with Clfa alone, one of the ten treated mice gave a negative response against Clfa fragment.

Immunization and Antibody Response Against ICHA I 014.

Female BALB/c mice were injected three times, at 2-week intervals with 50 μg ICHA I 014. HA and protein A (224-248) specific antibodies were detected by ELISA. Ninety-six-well microtiter plates were coated with 250 ng/50 μl of HA per well for the detection of antibodies against the carrier ICHA, and with 250 ng/50 μl of MBP-protein A (224-248) fragment fusion protein per well for the detection of antibodies against the protein A fragment. After washing, 150 μl of blocking buffer (casein hydrolysate) was added to each well and plates were incubated at 20° C. for 60 minutes. After washing with PBS containing 0.05% TWEEN 20®, serial two-fold dilution (starting at 1:50) of sera in blocking buffer were added and incubated for 1 h at 20° C.

The bound antibodies were detected by 30 minutes incubation at 20° C. with horseradish peroxidase (HRP)-labelled goat anti-mouse IgG. The reaction was developed using tetramethylbenzidine (TMB) during 3 minutes, the enzyme reaction was stopped by addition of 1M $H_2SO_4$ and the absorbance was read at 450 nm.

IgG antibody responses against the carrier and the protein A (224-248) fragment insert were plotted on graphs A and B of the FIG. 10. The results indicate that immunizations with ICHA 014 induce both anti-HA and anti-Protein A (224-248) specific antibodies. The panel C of FIG. 10 shows the percentage of immunized mice which develop a positive IgG anti-HA and anti-Protein A response at day 70.

A positive anti-HA IgG and anti-Protein A (224-248) response were observed 3 weeks (J21) after the first protein injection. The level of anti-Protein A (224-248) IgG was much lower than that of the antibody directed against the carrier protein. Nevertheless, we noted that the humoral response increased with the number of injections. Six weeks after the first injection the level of anti-Protein A (224-248) IgG was as high as that of the antibody directed against the carrier protein.

In order to evaluate the binding of the sera, obtained from the nine mice immunized with ICHA I 014, to the whole Protein A, we have developed an immunoassay. Protein A binds strongly to the constant region of the heavy chains of gamma-globulins, it is possible that false positive results may be obtained from non-specific binding of the antibodies to Protein A. To overcome this difficulty, Protein G-coated magnetic beads were used for the immobilization of sera immunoglobulins. Specific binding happened at the Fc part of the antibody, thus controlling its orientation and making its paratopes fully available to react with Protein A. Furthermore, the binding of the Protein G-magnetic beads to the constant region of the heavy chain did not interfere with the Protein A binding site on the antibodies, thereby allowing evaluation of the Protein A antibodies.

Protein G conjugated to magnetic beads was incubated with the different sera during 40 minutes at 20° C. Then, after the washing step that permits to remove the unbound antibodies, recombinant Protein A-biotin solution was allowed to bind for 60 minutes at 20° C. in a 50 μl final volume. After washing step, an incubation was performed with Steptavidine conjugated to the HRP. This incubation was done at 20° C. during 30 minutes. After the last washing step, TMB substrate solution was added to each well and the reaction were allowed to proceed for 3 minutes at 20° C. The reactions were stopped by adding 100 μl of 1M $H_2SO_4$. The absorbance of each well was determined using a microplate reader fitted with a 450 nm filter. Control wells contained sera obtained at J-1, magnetic bead-Protein G and Protein A-biotin.

The results obtained show that all the sera obtained from the immunization with ICHA I 014, contain a specific antibodies that interact with Protein A via their paratopes (FIG. 11).

Example 7

ICHA Polyepitopes Raise Antibodies Against the Inserts and HA in a Rabbit Model

The purified ICHA I 003 was used to immunize New Zeeland white rabbit. In this construction, two linear epitopes are displayed into ICHA. Because of their small sizes, these epitopes are not immunogenic if they are directly injected as a form corresponding to small peptides. Two hundred μg of ICHA I 003, each contained in 500 μl of PBS were mixed with an equal volume of complete Freund's adjuvant until a stable emulsion was obtained. One ml of this emulsion was used to immunize one rabbit. The rabbit was boosted with three additional immunizations at day 14, 28 and 56. Final bleeding was performed at day 72.

To verify the induction of antibodies against the carrier and the inserts after immunization with ICHA I 003, serotitration experiments were performed by incubating dilutions of the sera (preimmune serum and serum at day 72) with HA and two distinct MBP fusion proteins displaying the epitope SEB or TSST-1.

The serotitration curves are presented in FIG. 12. The data indicate that the injection of the polyepitope stimulates a humoral response against both the native *staphylococcal* alpha-hemolysin HA and the two heterologous epitopes (SEB and TSST-1) displayed on the carrier. In addition, the results on FIG. 13 show that the antibodies induced with ICHA I 003 neutralize completely the haemolytic activity of HA.

Example 8

Protection Against *S. aureus* Challenge by Active Immunization with ICHA Polytopes 8.1 Lethality Test In order to demonstrate the effect of ICHA and its derivatives in a vaccination against highly virulent *S. aureus* isolates, female BALB/c mice, 9 weeks old, were randomized into clean cages and quarantined for 7 days prior to study initiation. Groups of 5 or 10 animals each were immunized via subcutaneous route with 50 µl g of purified ICHA polytope, each contained in 230 µl of PBS, mixed with a volume of 20 µl QuilA adjuvant at a concentration of 1 mg/ml. Control mice received only PBS. The mice were boosted with two additional immunizations at day 21 and day 42 with the same amount of antigen or PBS. Blood samples were collected from both vaccinated and control groups before the beginning of the experiment (day 0) and the first 35 and 56 days. At day 56, mice were challenged intraperitoneally (IP) by $8.10^7$ CFU/ml of virulent *S. aureus* isolate 118. Post-challenge morbidity and mortality per individual group were recorded at 24 and 48 hours after challenge (in table 5 time of challenge is indicated by $T_o$). The survival data per individual treated group is outlined in table 5. In the table in the first column the number of animals per group is indicated in parenthesis.

TABLE 5

Survival of mice immunized with various ICHA polytope vaccines and challenge with virulent *S. aureus* strain 118.

| Groups | $T_0$ | +24 h | +48 h |
|---|---|---|---|
| PBS (10) | 100% | 0% | 0% |
| ICHA I 000-QuilA (5) | 100% | 100% | 100% |
| ICHA I 012-QuilA (10) | 100% | 94% | 74% |
| ICHA I 013-QuilA (10) | 100% | 87% | 54% |
| ICHA I 014-QuilA (10) | 100% | 38% | 25% |

All control mice infected with $8.10^7$ CFU died within 24 hours following the challenge. In contrast, in the group of mice (5) receiving ICHA I 000-QuilA, no death has occurred until 48 hours after the challenge. In addition, only 6% and 13% of the mice immunized with ICHA I 012-QuilA and ICHA I 013-QuilA respectively died within 24 hours after the challenge.

Mice that were administered Polytope ICHA I 012-QuilA, ICHA I 013-QuilA and ICHA I 014-QuilA showed 74%, 54% and 25% protection respectively 48 hours after the challenge.

8.2 Evolution of the Clinical Signs

The mice were monitored for clinical signs after 24 hours and 48 hours post-challenge. Disease severity was assessed using a 0 to 4 score (score 0: the mouse is in a fine shape, moves normally, eats and drinks normally and does not present abnormal behaviors; score 1: the mouse is dispirited, moves slowly, has dry hair, eats and drinks with difficulties; score 2: the mouse is very dispirited, no longer moves, has very dry hair, is no longer eats and drinks; score 3: the mouse is dying; and score 4: the mouse died). Table 6 shows the average of the scores observed in all mice of each group. In the table in the first column the number of animals per group is indicated in parenthesis.

TABLE 6

Average of the clinical scores observed in all the mice of each group immunized with ICHA polytope vaccines or PBS for the control group and challenge with virulent *S. aureus* strain 118.

| Groups | $T_0$ | +24 h | +48 h |
|---|---|---|---|
| PBS (10) | 0 | 4 | 4 |
| ICHA I 000-QuilA (5) | 0 | 2 | 3 |
| ICHA I 012-QuilA (10) | 0 | 1.3 | 2.3 |
| ICHA I 013-QuilA (10) | 0 | 1.7 | 3 |
| ICHA I 014-QuilA (10) | 0 | 3.12 | 3.25 |

The results show that the clinical signs observed related to the infection are less important in the four immunized groups. Among these 4 groups, 3 are those where less mortality is observed. Thus, 24 hours post-challenge, the groups immunized with the polytopes ICHA I 000, ICHA I 012-QuilA and ICHA I 013-QuilA present less severe clinical signs than the other groups.

In conclusion, control animals infected with *S. aureus* were highly susceptible and died rapidly compared with animals immunized with ICHA polytope vaccine. Animals immunized with ICHA I 000-QuilA, ICHA I 012-QuilA and ICHA I 013-QuilA displayed even fewer symptoms and signs of disease and less mortality.

8.3 Colonization of Internal Organs

Vaccine efficacy is conveniently expressed as the reduction in the number of CFU per kidney or spleen in vaccinated compared to control animals at selected times after challenge.

In order to determine whether the low mortality observed in the immunized mice was related to decreased bacterial burden in their organs, four groups of 20 BALB/c and one group of 5 mice (ICHA I 000-QuilA) each were immunized according to the protocols described before. Control mice received only PBS. At day 56, mice were challenged intraperitoneally with a sublethal dose ($2.3\ 10^7$ CFU/ml) of virulent *S. aureus* isolate 118.

Twenty-four hours after inoculation, the mice were euthanized and necropsied. The spleen and the kidney of each animal were then taken, weighed and homogenized with a homogenizer. Dilutions of homogenates were plated onto Chapman agar plates in triplicate. The plates were incubated at 37° C. for 24 hours, for bacteria counting. After incubation, the number of *S. aureus* colonies was enumerated and expressed as CFU per organ. Table 7 summarizes the CFU recovery from the tissues of mice of all the groups. In the table in the first column the number of animals per group is indicated in parenthesis.

TABLE 7

The CFU recovery from the tissues of mice of all the groups.

| | Spleen | | Kidney | |
|---|---|---|---|---|
| Groups | CFU count | Percent reduction | CFU count | Percent reduction |
| PBS (20) | 315 | 0% | 736 | 0% |
| ICHA I 000-QuilA (5) | 176 | 44% | 361 | 52% |
| ICHA I 012-QuilA (20) | 117 | 63% | 99 | 87% |
| ICHA I 013-QuilA (20) | 18 | 94% | 23 | 97% |
| ICHA I 014-QuilA (20) | 108 | 66% | 129 | 83% |

Bacteria recovery within the 24 hours post-challenge was approximately 2 fold higher in the spleen and in the kidney of the control mice challenged with *S. aureus* than in the organs of immunized mice by ICHA I 000 polytope.

The bacterial number declined in the 2 groups of animals immunized by ICHA I 012-QuilA, and ICHA I 014-QuilA. Decrease was much more pronounced in mice group immunized with ICHA I 013-QuilA, bacteria recovery was approximately 17-fold lower in the spleen, and 32-fold lower in the kidney of the mice immunized with ICHA I 013-QuilA polytope than in the control mice challenged with *S. aureus*.

Thus, active immunization targeting ICHA polytopes protects animals from *S. aureus* infection; this protection correlates with reduced microbiological colonization.

Conclusion.

In the studies of the present invention it was shown that the immunization with ICHA polytope conferred protection against *S. aureus* challenge in the mouse model of infection. This example demonstrated that an active protection against *S. aureus* could be achieved by administration of polytopes derived from recombinant ICHA proteins.

Example 9

Fragments of Protein A which Lack Binding to Fc and Fab Domain of Immunoglobulin G are Suitable Inserts for ICHA

*Staphylococcal* protein A (SpA) plays a key role in the pathogenicity of *S. aureus*. SpA is a protein of 42 kDa and comprises several regions with different functions (FIG. 14): the repeat region Wr, which are used for spa typing, the Wc region, which confers anchoring to the bacterial cell wall, the signal sequence (S region) in the N-terminal part and the four or five highly homologous immunoglobulin G (IgG)-binding domains, designated E, D, A, B, and C which share 65-90% amino acid sequence identity (FIG. 15). The Z domain of SpA reported in literature is an engineered analogue of the IgG-binding domain B. The size of these domains is relatively small; each contains ~58 amino acid residues. The solution structures of two of these domains, the B and E domains, as well as the very similar Z domain, have been determined by NMR spectroscopy. These structural analyses revealed that these IgG-binding domains adopted a classical "up-down" three-helical bundle fold. Cristallography and NMR studies indicated that the helix 1 and helix 2 interact with the Fc part of Ig while helix 2 and helix 3 bind to the Fab domain of Ig. These studies also indicated that the binding activity of SpA Ig-binding domains requires the presence of the three helices and is dependent of its 3D structure.

The binding activity of SpA acts to cloak the bacterial cell with IgG, thus blocking any interaction with Fc receptors on neutrophils and hindering phagocytosis. The capacity of SpA to bind the Fc part of immunoglobulins allows to escape the immune system and to cause a depletion of the B-cell repertoire.

Further, immunization assays performed by the present inventors by using ICHA I 009 confirmed that the display of a functional Ig-binding domain of SpA into ICHA did not trigger the induction of anti-SpA antibodies (data not shown). Engineering of SpA Derivatives Polyepitopes Related to ICHA I.

The heterologous SpA epitopes displayed into ICHA I are listed in table 2. The resulting polytopes are listed and described in table 3. The polyepitopes ICHA I 009, ICHA I 012, ICHA I 013 and ICHA I 014 corresponds to the full-length E domain (amino acid 187 to amino acid 248), helix 1 (aa 187-205), helix 2 (aa 206-223) and helix 3 (aa 224-248) of SpA, respectively. The four polyepitopes were produced and purified as described in example 3.

In order to further analyse the IgG-binding characteristics of the full immunoglobulin-binding domain and the three a-helices of the SpA domain, the four polyepitopes were tested for the recognition of mouse IgG antibody in ELISA experiments.

Microtitre ELISA plates (Nunc-Immuno Plate, Roskilde, Denmark) were coated with the four SpA derivatives ICHA polytopes (250 ng/well) in coating buffer (0.05 M carbonate-bicarbonate buffer, pH 9.6) and incubated overnight at 4° C. The protein ICHA I 000 was taken as control. The plates were washed three times with phosphate buffered saline containing 0.05% TWEEN 20®(PBST) and blocked with 150 µl of 3% casein hydrolysate in PBS for 1 h at 37° C. Mouse monoclonal antibody IgG anti-C1fA serially diluted 100 fold and 1000 fold in PBST were incubated in wells (50 µl/well) for 1 hour at 37° C. The wells were washed three times with PBST. The bound antibodies were detected by 1 hour incubation at 37° C. with horseradish peroxidase (HRP)-labelled goat anti-mouse IgG. The reaction was developed using tetramethyl-benzidine (TMB) during 10 minutes, the enzyme reaction was stopped by addition of 1M $H_2SO_4$ and the absorbance was read at 450 nm.

The ELISA reactivities of the SpA derivatives ICHA polytopes is shown in FIG. 16. These indicate that the E-domain of SpA displayed into ICHA (ICHA I 009) was still able to interact with IgG. In contrast, ICHA I 012, ICHA I 013, and ICHA I 014 were clearly unreactive. This indicates that the truncation of SpA Ig-binding domain was sufficient to abrogate IgG binding.

An important conclusion that could be drawn from these results is that SpA's capacity to interact with Fc region of immunoglobulin molecules was absent in the individual α-helix of the SpA domains.

In the studies of the present invention it was shown that the active vaccination with ICHA I 009 did not confer protection against *S. aureus* in challenge assays (data not shown). In contrast, the vaccination with ICHA I 012, ICHA I 013 and ICHA I 014 polytopes protected animals from *S. aureus* infection (see example 8).

What is claimed is:

1. A recombinant single-chain alpha-hemolysin polypeptide of *Staphylococcus aureus* comprising a deletion in the stem domain of the wild-type sequence of SEQ ID NO: 1 that removes hemolytic activity of the polypeptide, wherein at least one heterologous sequence is inserted in a region selected from the group consisting of regions defined by amino acid positions 108 to 151, amino acid positions 1 to 5, amino acid positions 288 to 293, amino acid positions 43 to 48, amino acid positions 235 to 240, amino acid positions 92 to 97, amino acid positions 31 to 36, and amino acid positions 156 to 161, each of SEQ ID NO: 1, with the proviso that, if the at least one heterologous sequence contains five or more consecutive histidine residues, a moiety of the at least one heterologous sequence other than a moiety comprising said five or more consecutive histidine residues, has a minimum length of 11 amino acid residues;

or an isolated variant polypeptide thereof, wherein in addition to said deletion in the stem domain and said insertion of the at least one heterologous sequence, 1 to 15 amino acid residues are added, or 1 to 15 amino acid residues in the SEQ ID NO: 1 are substituted or deleted and wherein the variant polypeptide has the activity to form oligomers and to bind to lipidic mono layers and lipidic bilayers, or cell membranes.

2. The recombinant alpha-hemolysin polypeptide according to claim 1, wherein the stem domain lies within the amino acid sequence from Thr109 to Gln150 of the wild-type sequence of SEQ ID NO: 1 and is partially or completely deleted.

3. The recombinant alpha-hemolysin polypeptide according to claim 1, wherein the heterologous sequence has a minimum of 5 continuous amino acid residues.

4. The recombinant alpha-hemolysin polypeptide of claim 1, which comprises at least two of the heterologous sequences inserted in the same insertion sites or inserted in different insertion sites.

5. The recombinant alpha-hemolysin polypeptide according to claim 1, wherein the at least one heterologous sequence is from *Staphylococcus* species.

6. The recombinant alpha-hemolysin polypeptide according to claim 5, wherein the at least one heterologous sequence is selected from the group consisting of *Staphylococcus aureus* enterotoxin B (SEB), toxic shock syndrome toxin (TSST), fibronectin-binding protein (FnBP), beta-lactamase, Clumping Factor A (ClfA), penicillin-binding protein 2a (PBP2a), and Protein A.

7. The recombinant alpha-hemolysin polypeptide according to claim 1, wherein the alpha-hemolysin polypeptide comprises the sequence of SEQ ID NO: 3, or the sequence of SEQ ID NO: 5, or an isolated polypeptide variant having 95% or more amino acid sequence identity to the sequence of SEQ ID NO: 3 or to the sequence of SEQ ID NO: 5.

8. An immunogenic composition comprising a recombinant single-chain alpha-hemolysin polypeptide of *Staphylococcus aureus* comprising a deletion in the stem domain of the wild-type sequence of SEQ ID NO: 1 that removes hemolytic activity of the polypeptide, wherein at least one heterologous sequence from *Staphylococcus* species is inserted in a solvent-exposed loop of SEQ ID NO: 1, or an isolated variant polypeptide thereof, wherein in addition to said deletion in the stem domain and said insertion of the at least one heterologous sequence, 1 to 15 amino acid residues are added, or 1 to 15 amino acid residues in the SEQ ID NO: 1 are substituted or deleted and wherein the variant polypeptide has the activity to form oligomers and to bind to lipidic mono layers and lipidic bilayers, or cell membranes.

9. The immunogenic composition according to claim 8, wherein the at least one heterologous sequence is inserted in a region selected from the group consisting of regions defined by amino acid positions 108 to 151, amino acid positions 1 to 5, amino acid positions 288to 293, amino acid positions 43 to 48, amino acid positions 235 to 240, amino acid positions 92to 97, amino acid positions 31 to 36, and amino acid positions 156 to 161, each of the wild-type sequence of SEQ ID NO: 1.

10. A recombinant single-chain alpha-hemolysin polypeptide of *Staphylococcus aureus* comprising a deletion in the stem domain of the wild-type sequence of SEQ ID NO: 1 that removes hemolytic activity of the polypeptide, wherein at least one heterologous sequence is inserted into a permissive site, and the at least one heterologous sequence comprises a fragment of an immunoglobulin G-binding domain of a full-length Protein A of *Staphylococcus* species, wherein the fragment comprises a minimum of five continuous amino acids of said domain;
  or an isolated variant polypeptide thereof, wherein in addition to said deletion in the stem domain and said insertion of the at least one heterologous sequence, 1 to 15 amino acid residues are added, or 1 to 15 amino acid residues in the SEQ ID NO: 1 are substituted or deleted and wherein the variant polypeptide has the activity to form oligomers and to bind to lipidic mono layers and lipidic bilayers, or cell membranes.

11. The recombinant alpha-hemolysin polypeptide according to claim 10, wherein the fragment of the immunoglobulin G-binding domain of the Protein A comprises 5 to 35contiguous amino acid residues of said domain.

12. The recombinant alpha-hemolysin polypeptide according to claim 10, wherein the fragment of the immunoglobulin G-binding domain of the Protein A covers not more than two complete alpha-helices of the domain.

13. The recombinant alpha-hemolysin polypeptide according to claim 10, wherein the permissive site is located within a solvent-exposed loop of SEQ ID NO: 1.

14. The recombinant alpha-hemolysin polypeptide according to claim 10, wherein the stem domain lies within the amino acid sequence from Thr109 to Gln150 of the wild-type sequence of SEQ ID NO: 1 and is partially or completely deleted.

15. The recombinant alpha-hemolysin polypeptide according to claim 10, wherein the alpha-hemolysin polypeptide comprises the sequence of SEQ ID NO: 3, the sequence of SEQ ID NO: 5, or a polypeptide variant having 95% or more amino acid sequence identity to the sequence of SEQ ID NO: 3 or to the sequence of SEQ ID NO: 5.

16. An immunogenic composition comprising a recombinant single-chain alpha-hemolysin polypeptide of *Staphylococcus aureus* comprising a deletion in the stem domain of the wild-type sequence of SEQ ID NO: 1 that removes hemolytic activity of the polypeptide, wherein at least one heterologous sequence is inserted in a solvent-exposed loop of SEQ ID NO: 1 and the at least one heterologous sequence comprises a fragment of an immunoglobulin G-binding domain of a full-length Protein A of *Staphylococcus* species, wherein the fragment comprises a minimum of five continuous amino acid residues of the domain and has no binding or reduced binding to Fc or Fab domain of immunoglobulin G compared to the full-length Protein A;
  or an isolated variant polypeptide thereof, wherein in addition to said deletion in the stem domain and said insertion of the at least one heterologous sequence, 1 to 15 amino acid residues are added, or 1 to 15 amino acid residues in the SEQ ID NO: 1 are substituted or deleted, and wherein the variant polypeptide has the activity to form oligomers and to bind to lipidic mono layers and lipidic bilayers, or cell membranes.

\* \* \* \* \*

SEQUENCE LISTING

<160> NUMBER OF SEQ ID NOS: 79

<210> SEQ ID NO 1
<211> LENGTH: 293
<212> TYPE: PRT
<213> ORGANISM: Staphylococcus aureus
<220> FEATURE:
<221> NAME/KEY: PEPTIDE
<222> LOCATION: (1)..(293)
<223> OTHER INFORMATION: wild-type alpha-hemolysin

<400> SEQUENCE: 1

```
Ala Asp Ser Asp Ile Asn Ile Lys Thr Gly Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
                35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
                115                 120                 125

Thr Gly Lys Ile Gly Gly Leu Ile Gly Ala Asn Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 2
<211> LENGTH: 879
<212> TYPE: DNA
<213> ORGANISM: Staphylococcus aureus
<220> FEATURE:
<221> NAME/KEY: gene
<222> LOCATION: (1)..(879)
<223> OTHER INFORMATION: gene encoding wild-type alpha-hemolysin

<400> SEQUENCE: 2

```
gcagattctg atattaatat aaaaccggt actacagata ttggaagcaa tactacagta      60
aaaacaggtg atttagtcac ttatgataaa gaaaatggca tgcacaaaaa agtattttat    120
agttttatcg atgataaaaa tcacaataaa aaactgctag ttattagaac gaaaggtacc    180
attgctggtc aatatagagt ttatagcgaa gaaggtgcta acaaaagtgg tttagcctgg    240
```

-continued

```
ccttcagcct ttaaggtaca gttgcaacta cctgataatg aagtagctca aatatctgat    300
tactatccaa gaaattcgat tgatacaaaa gagtatatga gtactttaac ttatggattc    360
aacggtaatg ttactggtga tgatacagga aaaattggcg gccttattgg tgcaaatgtt    420
tcgattggtc atacactgaa atatgttcaa cctgatttca aaacaatttt agagagccca    480
actgataaaa aagtaggctg gaaagtgata tttaacaata tggtgaatca aaattgggga    540
ccatatgata gagattcttg gaacccggta tatggcaatc aacttttcat gaaaactaga    600
aatggttcta tgaaagcagc agataacttc cttgatccta acaaagcaag ttctctatta    660
tcttcagggt tttcaccaga cttcgctaca gttattacta tggatagaaa agcatccaaa    720
caacaaacaa atatagatgt aatatacgaa cgagttcgtg atgattacca attgcattgg    780
acttcaacaa attggaaagg taccaatact aaagataaat ggacagatcg ttcttcagaa    840
agatataaaa tcgattggga aaaagaagaa atgacaaat                           879
```

<210> SEQ ID NO 3
<211> LENGTH: 257
<212> TYPE: PRT
<213> ORGANISM: Artificial
<220> FEATURE:
<223> OTHER INFORMATION: mutated alpha-hemolysin (ICHA I)
<220> FEATURE:
<221> NAME/KEY: peptide
<222> LOCATION: (1)..(257)
<223> OTHER INFORMATION: mutated alpha-hemolysin (ICHA I)

<400> SEQUENCE: 3

```
Met Ala Asp Ser Asp Ile Asn Ile Lys Thr Gly Thr Thr Asp Ile Gly
1               5                   10                  15

Ser Asn Thr Thr Val Lys Thr Gly Gly Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Thr
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Pro Gly Asn
            100                 105                 110

Pro Asp Phe Lys Thr Ile Leu Glu Ser Pro Thr Asp Lys Lys Val Gly
        115                 120                 125

Trp Lys Val Ile Phe Asn Asn Met Val Asn Gln Asn Trp Gly Pro Tyr
    130                 135                 140

Asp Arg Asp Ser Trp Asn Pro Val Tyr Gly Asn Gln Leu Phe Met Lys
145                 150                 155                 160

Thr Arg Asn Gly Ser Met Lys Ala Ala Asp Asn Phe Leu Asp Pro Asn
                165                 170                 175

Lys Ala Ser Ser Leu Leu Ser Ser Gly Phe Ser Pro Asp Phe Ala Thr
            180                 185                 190

Val Ile Thr Met Asp Arg Lys Ala Ser Lys Gln Gln Thr Asn Ile Asp
        195                 200                 205

Val Ile Tyr Glu Arg Val Arg Asp Asp Tyr Gln Leu His Trp Thr Ser
    210                 215                 220

Thr Asn Trp Lys Gly Thr Asn Thr Lys Asp Lys Trp Ile Asp Arg Ser
225                 230                 235                 240
```

Ser Glu Arg Tyr Lys Ile Asp Trp Glu Lys Glu Glu Met Thr Asn Lys
            245                 250                 255

Leu

<210> SEQ ID NO 4
<211> LENGTH: 771
<212> TYPE: DNA
<213> ORGANISM: Artificial
<220> FEATURE:
<223> OTHER INFORMATION: gene encoding mutated alpha-hemolysin (ICHA I)

<400> SEQUENCE: 4

```
atggcagatt ctgatattaa tattaaaacc ggtactacag atattggaag caatactaca     60
gtaaaaacag gtggtttagt cacttatgat aaagaaaatg gcatgcacaa aaaagtattt    120
tatagttta tcgatgataa aaatcataat aaaaaactgc tagttattag aacgaaaggt    180
accattgctg gtcaatatag agtttatagc gaagaaggtg ctaacaaaag tggtttaacc    240
tggccttcag ccttttaaggt acagttgcaa ctacctgata tgaagtagc tcaaatatct    300
gattactatc caagaaattc gattgatccc gggaaccctg atttcaaaac aattttagag    360
agcccaactg ataaaaagt aggctggaaa gtgatattta caatatggt gaatcaaaat    420
tggggaccat atgatagaga ttcttggaac ccggtatatg caatcaact tttcatgaaa    480
actagaaatg gctctatgaa agcagcagat aacttccttg atcctaacaa agcaagttct    540
ctattatctt cagggttttc accagacttc gctacagtta ttactatgga tagaaaagca    600
tccaaacaac aaacaaatat agatgtaata tacgaacgag ttcgtgatga ctaccaattg    660
cactggactt caacaaattg gaaggtacc aatactaaag ataaatggat agatcgttct    720
tcagaaagat ataaaatcga ttgggaaaaa gaagaaatga caaataagct t            771
```

<210> SEQ ID NO 5
<211> LENGTH: 267
<212> TYPE: PRT
<213> ORGANISM: Artificial
<220> FEATURE:
<223> OTHER INFORMATION: mutated alpha-hemolysin (ICHA II)

<400> SEQUENCE: 5

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Ser Gly Met His Lys Lys Val Phe Tyr Ser Phe Ile Asp Asp
        35                  40                  45

Leu Gln Lys Asn His Asn Lys Lys Leu Leu Val Ile Arg Thr Lys Gly
    50                  55                  60

Thr Ile Ala Gly Gln Tyr Arg Val Tyr Ser Glu Glu Gly Ala Asn Lys
65                  70                  75                  80

Ser Gly Leu Thr Trp Pro Ser Ala Phe Lys Val Gln Leu Gln Leu Pro
                85                  90                  95

Asp Asn Glu Glu Leu Val Ala Gln Ile Ser Asp Tyr Tyr Pro Arg Asn
            100                 105                 110

Ser Ile Asp Pro Gly Asn Pro Asp Phe Lys Thr Ile Leu Glu Phe Glu
        115                 120                 125

Ser Pro Thr Asp Lys Lys Val Gly Trp Lys Val Ile Phe Asn Asn Met
    130                 135                 140

Val Asn Gln Asn Trp Gly Pro Tyr Asp Arg Asp Ser Trp Asn Pro Val

```
                145                 150                 155                 160
Tyr Gly Asn Gln Leu Phe Met Lys Thr Arg Asn Gly Ser Met Lys Ala
                    165                 170                 175
Ala Asp Asn Phe Leu Asp Pro Asn Lys Ala Ser Ser Leu Leu Ser Ser
                    180                 185                 190
Gly Phe Ser Pro Asp Phe Ala Thr Val Ile Thr Met Asp Arg Lys Ala
                    195                 200                 205
Ser Ala Ser Lys Gln Gln Thr Asn Ile Asp Val Ile Tyr Glu Arg Val
                    210                 215                 220
Arg Asp Asp Tyr Gln Leu His Trp Thr Ser Thr Asn Trp Lys Gly Thr
225                 230                 235                 240
Asn Thr Lys Asp Lys Trp Ile Asp Arg Ser Ser Glu Arg Tyr Lys Ile
                    245                 250                 255
Asp Trp Glu Lys Glu Glu Met Thr Asn Lys Leu
                    260                 265

<210> SEQ ID NO 6
<211> LENGTH: 801
<212> TYPE: DNA
<213> ORGANISM: Artificial
<220> FEATURE:
<223> OTHER INFORMATION: gene encoding mutated alpha-hemolysin (ICHA II)

<400> SEQUENCE: 6
atggcagatt ctgatattaa tattaaaacc ggtactacag atattggaag caatactaca      60
gtaaaaacag gtgatttagt cacttatgat aaagaaatg gatccggcat gcacaaaaaa     120
gtattttata gttttatcga tgatctgcag aaaaatcata taaaaaaact gctagttatt     180
agaacgaaag gtaccattgc tggtcaatat agagtttata gcgaagaagg tgctaacaaa     240
agtggtttaa cctggccttc agcctttaag gtacagttgc aactacctga taatgaagag     300
ctcgtagctc aaatatctga ttactatcca agaaattcga ttgatcccgg aaccctgat      360 ttcaaaacaa ttttagaatt cgagagccca actgataaaa aagtaggctg aaagtgata      420 tttaacaata tggtgaatca aaattgggga ccatatgata gagattcttg aacccggta      480 tatggcaatc aactttttcat gaaaactaga atggctcta tgaaagcagc agataacttc     540
cttgatccta caaagcaag ttctctatta tcttcagggt tttcaccaga cttcgctaca     600
gttattacta tggatagaaa agctagcgca tccaaacaac aaacaaatat agatgtaata     660
tacgaacgag ttcgtgatga ctaccaattg cactggactt caacaaattg gaaaggtacc     720
aatactaaag ataaatggat agatcgttct tcagaaagat ataaaatcga ttgggaaaaa     780
gaagaaatga caaataagct t                                              801

<210> SEQ ID NO 7
<211> LENGTH: 10
<212> TYPE: PRT
<213> ORGANISM: Artificial
<220> FEATURE:
<223> OTHER INFORMATION: synthetic peptide

<400> SEQUENCE: 7

Lys Lys Lys Val Thr Ala Gln Glu Leu Asp
1               5                  10

<210> SEQ ID NO 8
<211> LENGTH: 16
<212> TYPE: PRT
<213> ORGANISM: Artificial
<220> FEATURE:
```

```
<223> OTHER INFORMATION: synthetic peptide

<400> SEQUENCE: 8

Gln Thr Asn Lys Lys Val Thr Ala Gln Glu Leu Asp Tyr Leu Thr
1               5                   10                  15

<210> SEQ ID NO 9
<211> LENGTH: 15
<212> TYPE: PRT
<213> ORGANISM: Artificial
<220> FEATURE:
<223> OTHER INFORMATION: synthetic peptide

<400> SEQUENCE: 9

Phe Pro Ser Pro Tyr Tyr Ser Pro Ala Phe Thr Lys Gly Glu Lys
1               5                   10                  15

<210> SEQ ID NO 10
<211> LENGTH: 76
<212> TYPE: PRT
<213> ORGANISM: Artificial
<220> FEATURE:
<223> OTHER INFORMATION: synthtic peptide

<400> SEQUENCE: 10

Gly Met Ser Asn Glu Glu Tyr Asn Lys Leu Thr Glu Asp Lys Lys Glu
1               5                   10                  15

Pro Leu Leu Asn Lys Phe Gln Ile Thr Thr Ser Pro Gly Ser Thr Gln
                20                  25                  30

Lys Ile Leu Thr Ala Met Ile Gly Leu Asn Asn Lys Thr Leu Asp Asp
            35                  40                  45

Lys Thr Ser Tyr Lys Ile Asp Gly Lys Gly Trp Gln Lys Asp Lys Ser
        50                  55                  60

Trp Gly Gly Tyr Asn Val Thr Arg Tyr Glu Val Val
65                  70                  75

<210> SEQ ID NO 11
<211> LENGTH: 57
<212> TYPE: PRT
<213> ORGANISM: Artificial
<220> FEATURE:
<223> OTHER INFORMATION: synthetic peptide

<400> SEQUENCE: 11

Gly Gly Ile Lys Lys Val Lys Gln Arg Leu Lys Glu Leu Gly Asp Lys
1               5                   10                  15

Val Thr Asn Pro Val Arg Tyr Glu Ile Glu Leu Asn Tyr Tyr Ser Pro
                20                  25                  30

Lys Ser Lys Lys Asp Thr Ser Thr Pro Ala Ala Phe Gly Lys Thr Leu
            35                  40                  45

Asn Lys Leu Ile Ala Asn Gly Lys Leu
        50                  55

<210> SEQ ID NO 12
<211> LENGTH: 17
<212> TYPE: PRT
<213> ORGANISM: Artificial
<220> FEATURE:
<223> OTHER INFORMATION: synthetic peptide

<400> SEQUENCE: 12

Lys Tyr Glu Gln Gly Gly Asn Ile Val Asp Ile Asp Phe Asp Ser Val
1               5                   10                  15
```

Pro

<210> SEQ ID NO 13
<211> LENGTH: 13
<212> TYPE: PRT
<213> ORGANISM: Artificial
<220> FEATURE:
<223> OTHER INFORMATION: synthetic peptide

<400> SEQUENCE: 13

Gln Phe Gly Gly His Asn Ser Val Asp Phe Glu Asp Thr
1               5                   10

<210> SEQ ID NO 14
<211> LENGTH: 59
<212> TYPE: PRT
<213> ORGANISM: Artificial
<220> FEATURE:
<223> OTHER INFORMATION: synthetic peptide

<400> SEQUENCE: 14

Gly Asp Leu Ala Leu Arg Ser Thr Phe Tyr Gly Tyr Asn Ser Asn Ile
1               5                   10                  15

Ile Trp Arg Ser Met Ser Trp Asp Asn Glu Val Ala Phe Asn Asn Gly
            20                  25                  30

Ser Gly Ser Gly Asp Gly Ile Asp Lys Pro Val Val Pro Glu Gln Pro
        35                  40                  45

Asp Glu Pro Gly Glu Ile Glu Pro Ile Pro Glu
    50                  55

<210> SEQ ID NO 15
<211> LENGTH: 62
<212> TYPE: PRT
<213> ORGANISM: Artificial
<220> FEATURE:
<223> OTHER INFORMATION: synthetic peptide

<400> SEQUENCE: 15

Asn Lys Phe Asn Lys Glu Gln Gln Asn Ala Phe Tyr Glu Ile Leu His
1               5                   10                  15

Leu Pro Asn Leu Thr Glu Glu Gln Arg Asn Gly Phe Ile Gln Ser Leu
            20                  25                  30

Lys Asp Asp Pro Ser Val Ser Lys Glu Ile Leu Ala Glu Ala Lys Lys
        35                  40                  45

Leu Asn Asp Ala Gln Ala Pro Lys Glu Glu Asp Asn Lys Lys
    50                  55                  60

<210> SEQ ID NO 16
<211> LENGTH: 19
<212> TYPE: PRT
<213> ORGANISM: Artificial
<220> FEATURE:
<223> OTHER INFORMATION: synthetic peptide

<400> SEQUENCE: 16

Asn Lys Phe Asn Lys Glu Gln Gln Asn Ala Phe Tyr Glu Ile Leu His
1               5                   10                  15

Leu Pro Asn

<210> SEQ ID NO 17
<211> LENGTH: 18
<212> TYPE: PRT
<213> ORGANISM: Artificial
<220> FEATURE:

<223> OTHER INFORMATION: synthetic peptide

<400> SEQUENCE: 17

Leu Thr Glu Glu Gln Arg Asn Gly Phe Ile Gln Ser Leu Lys Asp Asp
1               5                   10                  15

Pro Ser

<210> SEQ ID NO 18
<211> LENGTH: 25
<212> TYPE: PRT
<213> ORGANISM: Artificial
<220> FEATURE:
<223> OTHER INFORMATION: synthetic peptide

<400> SEQUENCE: 18

Val Ser Lys Glu Ile Leu Ala Glu Ala Lys Lys Leu Asn Asp Ala Gln
1               5                   10                  15

Ala Pro Lys Glu Glu Asp Asn Lys Lys
            20                  25

<210> SEQ ID NO 19
<211> LENGTH: 5
<212> TYPE: PRT
<213> ORGANISM: Artificial
<220> FEATURE:
<223> OTHER INFORMATION: synthetic peptide

<400> SEQUENCE: 19

Ala Asp Ser Asp Ile
1               5

<210> SEQ ID NO 20
<211> LENGTH: 6
<212> TYPE: PRT
<213> ORGANISM: Artificial
<220> FEATURE:
<223> OTHER INFORMATION: synthetic peptide

<400> SEQUENCE: 20

Met Ala Asp Ser Asp Ile
1               5

<210> SEQ ID NO 21
<211> LENGTH: 6
<212> TYPE: PRT
<213> ORGANISM: Artificial
<220> FEATURE:
<223> OTHER INFORMATION: synthetic peptide

<400> SEQUENCE: 21

Lys Glu Asn Gly Met His
1               5

<210> SEQ ID NO 22
<211> LENGTH: 8
<212> TYPE: PRT
<213> ORGANISM: Artificial
<220> FEATURE:
<223> OTHER INFORMATION: synthetic peptide

<400> SEQUENCE: 22

Lys Glu Asn Gly Ser Gly Met His
1               5

<210> SEQ ID NO 23
<211> LENGTH: 6

```
<212> TYPE: PRT
<213> ORGANISM: Artificial
<220> FEATURE:
<223> OTHER INFORMATION: synthetic peptide

<400> SEQUENCE: 23

Ile Asp Asp Lys Asn His
1               5

<210> SEQ ID NO 24
<211> LENGTH: 8
<212> TYPE: PRT
<213> ORGANISM: Artificial
<220> FEATURE:
<223> OTHER INFORMATION: synthetic peptide

<400> SEQUENCE: 24

Ile Asp Asp Leu Gln Lys Asn His
1               5

<210> SEQ ID NO 25
<211> LENGTH: 6
<212> TYPE: PRT
<213> ORGANISM: Artificial
<220> FEATURE:
<223> OTHER INFORMATION: synthetic peptide

<400> SEQUENCE: 25

Asp Asn Glu Val Ala Gln
1               5

<210> SEQ ID NO 26
<211> LENGTH: 8
<212> TYPE: PRT
<213> ORGANISM: Artificial
<220> FEATURE:
<223> OTHER INFORMATION: synthetic peptide

<400> SEQUENCE: 26

Asp Asn Glu Glu Leu Val Ala Gln
1               5

<210> SEQ ID NO 27
<211> LENGTH: 9
<212> TYPE: PRT
<213> ORGANISM: Artificial
<220> FEATURE:
<223> OTHER INFORMATION: synthetic peptide

<400> SEQUENCE: 27

Ser Ile Asp Pro Gly Asn Pro Asp Phe
1               5

<210> SEQ ID NO 28
<211> LENGTH: 6
<212> TYPE: PRT
<213> ORGANISM: Artificial
<220> FEATURE:
<223> OTHER INFORMATION: synthetic peptide

<400> SEQUENCE: 28

Thr Ile Leu Glu Ser Pro
1               5

<210> SEQ ID NO 29
<211> LENGTH: 8
<212> TYPE: PRT
<213> ORGANISM: Artificial
```

```
<220> FEATURE:
<223> OTHER INFORMATION: synthetic peptide

<400> SEQUENCE: 29

Thr Ile Leu Glu Phe Glu Ser Pro
1               5

<210> SEQ ID NO 30
<211> LENGTH: 6
<212> TYPE: PRT
<213> ORGANISM: Artificial
<220> FEATURE:
<223> OTHER INFORMATION: synthetic peptide

<400> SEQUENCE: 30

Asp Arg Lys Ala Ser Lys
1               5

<210> SEQ ID NO 31
<211> LENGTH: 8
<212> TYPE: PRT
<213> ORGANISM: Artificial
<220> FEATURE:
<223> OTHER INFORMATION: synthetic peptide

<400> SEQUENCE: 31

Asp Arg Lys Ala Ser Ala Ser Lys
1               5

<210> SEQ ID NO 32
<211> LENGTH: 6
<212> TYPE: PRT
<213> ORGANISM: Artificial
<220> FEATURE:
<223> OTHER INFORMATION: artificial peptide

<400> SEQUENCE: 32

Lys Glu Glu Met Thr Asn
1               5

<210> SEQ ID NO 33
<211> LENGTH: 8
<212> TYPE: PRT
<213> ORGANISM: Artificial
<220> FEATURE:
<223> OTHER INFORMATION: artificial peptide

<400> SEQUENCE: 33

Lys Glu Glu Met Thr Asn Lys Leu
1               5

<210> SEQ ID NO 34
<211> LENGTH: 46
<212> TYPE: DNA
<213> ORGANISM: Artificial
<220> FEATURE:
<223> OTHER INFORMATION: synthetic primer

<400> SEQUENCE: 34
ggccatggca gattctgata ttaatattaa aaccggtact acagat          46

<210> SEQ ID NO 35
<211> LENGTH: 44
<212> TYPE: DNA
<213> ORGANISM: Artificial
<220> FEATURE:
<223> OTHER INFORMATION: synthetic primer
```

```
<400> SEQUENCE: 35
gcaagcttat tgtcatttc ttcttttcc caatcgattt tata                    44

<210> SEQ ID NO 36
<211> LENGTH: 42
<212> TYPE: DNA
<213> ORGANISM: Artificial
<220> FEATURE:
<223> OTHER INFORMATION: synthetic primer

<400> SEQUENCE: 36
gatcccggga accctgattt caaaacaatt ttagagagcc ca                    42

<210> SEQ ID NO 37
<211> LENGTH: 63
<212> TYPE: DNA
<213> ORGANISM: Artificial
<220> FEATURE:
<223> OTHER INFORMATION: synthetic primer

<400> SEQUENCE: 37
aattgttttg aaatcagggt tcccgggatc aatcgaattt cttggatagt aatcagatat    60
ttg                                                                  63

<210> SEQ ID NO 38
<211> LENGTH: 36
<212> TYPE: DNA
<213> ORGANISM: Artificial
<220> FEATURE:
<223> OTHER INFORMATION: synthetic primer

<400> SEQUENCE: 38
tatgataaag aaaatggatc cggcatgcac aaaaaa                            36

<210> SEQ ID NO 39
<211> LENGTH: 36
<212> TYPE: DNA
<213> ORGANISM: Artificial
<220> FEATURE:
<223> OTHER INFORMATION: synthetic primer

<400> SEQUENCE: 39 tttttgtgc atgccggatc cattttcttt atcata                             36

<210> SEQ ID NO 40
<211> LENGTH: 36
<212> TYPE: DNA
<213> ORGANISM: Artificial
<220> FEATURE:
<223> OTHER INFORMATION: synthetic primer

<400> SEQUENCE: 40
agttttatcg atgatctgca gaaaaatcat aataaa                            36

<210> SEQ ID NO 41
<211> LENGTH: 36
<212> TYPE: DNA
<213> ORGANISM: Artificial
<220> FEATURE:
<223> OTHER INFORMATION: synthetic primer

<400> SEQUENCE: 41
tttattatga tttttctgca gatcatcgat aaaact                            36

<210> SEQ ID NO 42
```

```
<211> LENGTH: 36
<212> TYPE: DNA
<213> ORGANISM: Artificial
<220> FEATURE:
<223> OTHER INFORMATION: synthetic primer

<400> SEQUENCE: 42
ttcaaaacaa ttttagaatt cgagagccca actgat                    36

<210> SEQ ID NO 43
<211> LENGTH: 36
<212> TYPE: DNA
<213> ORGANISM: Artificial
<220> FEATURE:
<223> OTHER INFORMATION: synthetic primer

<400> SEQUENCE: 43
atcagttggg ctctcgaatt ctaaaattgt tttgaa                    36

<210> SEQ ID NO 44
<211> LENGTH: 36
<212> TYPE: DNA
<213> ORGANISM: Artificial
<220> FEATURE:
<223> OTHER INFORMATION: synthetic primer

<400> SEQUENCE: 44
actatggata gaaaagctag cgcatccaaa caacaa                    36

<210> SEQ ID NO 45
<211> LENGTH: 36
<212> TYPE: DNA
<213> ORGANISM: Artificial
<220> FEATURE:
<223> OTHER INFORMATION: synthetic primer

<400> SEQUENCE: 45
ttgttgtttg gatgcgctag cttttctatc catagt                    36

<210> SEQ ID NO 46
<211> LENGTH: 36
<212> TYPE: DNA
<213> ORGANISM: Artificial
<220> FEATURE:
<223> OTHER INFORMATION: synthetic primer

<400> SEQUENCE: 46
ttgcactgga cttcagagct cacaaattgg aaaggt                    36

<210> SEQ ID NO 47
<211> LENGTH: 36
<212> TYPE: DNA
<213> ORGANISM: Artificial
<220> FEATURE:
<223> OTHER INFORMATION: synthetic primer

<400> SEQUENCE: 47
acctttccaa tttgtgagct ctgaagtcca gtgcaa                    36

<210> SEQ ID NO 48
<211> LENGTH: 45
<212> TYPE: DNA
<213> ORGANISM: Artificial
<220> FEATURE:
<223> OTHER INFORMATION: synthetic primer

<400> SEQUENCE: 48
```

```
ggatgggcaa aagaaagtg acagcgcagg agcttgacgc catgg              45

<210> SEQ ID NO 49
<211> LENGTH: 45
<212> TYPE: DNA
<213> ORGANISM: Artificial
<220> FEATURE:
<223> OTHER INFORMATION: synthetic primer

<400> SEQUENCE: 49
ccatggcgtc aagctcctgc gctgtcactt tctttttgcc catgg              45

<210> SEQ ID NO 50
<211> LENGTH: 54
<212> TYPE: DNA
<213> ORGANISM: Artificial
<220> FEATURE:
<223> OTHER INFORMATION: synthetic primer

<400> SEQUENCE: 50 aagcttttc cgagtcctta ttatagccct gcttttacaa aaggggaaaa gctt     54

<210> SEQ ID NO 51
<211> LENGTH: 54
<212> TYPE: DNA
<213> ORGANISM: Artificial
<220> FEATURE:
<223> OTHER INFORMATION: synthetic primer

<400> SEQUENCE: 51
aagcttttcc cctttttgtaa aagcagggct ataataagga ctcggaaaaa gctt   54

<210> SEQ ID NO 52
<211> LENGTH: 36
<212> TYPE: DNA
<213> ORGANISM: Artificial
<220> FEATURE:
<223> OTHER INFORMATION: synthetic primer

<400> SEQUENCE: 52
tttcttggtg atttagcact acgttcgaca ttttat                       36

<210> SEQ ID NO 53
<211> LENGTH: 36
<212> TYPE: DNA
<213> ORGANISM: Artificial
<220> FEATURE:
<223> OTHER INFORMATION: synthetic primer

<400> SEQUENCE: 53
tggtagctct ggaatgggtt caatttcacc aggctc                       36

<210> SEQ ID NO 54
<211> LENGTH: 60
<212> TYPE: DNA
<213> ORGANISM: Artificial
<220> FEATURE:
<223> OTHER INFORMATION: synthetic primer

<400> SEQUENCE: 54
aagcttcaaa ctaataagaa aaaggtgact gctcaagaat tagattacct aactaagctt   60

<210> SEQ ID NO 55
<211> LENGTH: 60
<212> TYPE: DNA
<213> ORGANISM: Artificial
<220> FEATURE:
```

<223> OTHER INFORMATION: synthetic primer

<400> SEQUENCE: 55
aagcttagtt aggtaatcta attcttgagc agtcaccttt ttcttattag tttgaagctt    60

<210> SEQ ID NO 56
<211> LENGTH: 102
<212> TYPE: DNA
<213> ORGANISM: Artificial
<220> FEATURE:
<223> OTHER INFORMATION: synthetic primer

<400> SEQUENCE: 56
tggtcgaaat atgaacaagg tggcaatatt gtagatatcg atttcgacag tgtacctcaa    60
ttcggtggac acaatagtgt tgactttgaa gatacacgtc aa                       102

<210> SEQ ID NO 57
<211> LENGTH: 102
<212> TYPE: DNA
<213> ORGANISM: Artificial
<220> FEATURE:
<223> OTHER INFORMATION: synthetic primer

<400> SEQUENCE: 57
ttgacgtgta tcttcaaagt caacactatt gtgtccaccg aattgaggta cactgtcgaa    60
atcgatatct acaatattgc caccttgttc atatttcgac ca                       102

<210> SEQ ID NO 58
<211> LENGTH: 36
<212> TYPE: DNA
<213> ORGANISM: Artificial
<220> FEATURE:
<223> OTHER INFORMATION: synthetic primer

<400> SEQUENCE: 58
tgtgcgggca tgagtaacga agaatataat aaatta                              36

<210> SEQ ID NO 59
<211> LENGTH: 36
<212> TYPE: DNA
<213> ORGANISM: Artificial
<220> FEATURE:
<223> OTHER INFORMATION: synthetic primer

<400> SEQUENCE: 59
cccacatacc acttcatagc gtgtaacgtt gtaacc                              36

<210> SEQ ID NO 60
<211> LENGTH: 36
<212> TYPE: DNA
<213> ORGANISM: Artificial
<220> FEATURE:
<223> OTHER INFORMATION: synthetic primer

<400> SEQUENCE: 60
ggtggaatca aaaagttaa acaacgtcta aagaa                                36

<210> SEQ ID NO 61
<211> LENGTH: 39
<212> TYPE: DNA
<213> ORGANISM: Artificial
<220> FEATURE:
<223> OTHER INFORMATION: synthetic primer

<400> SEQUENCE: 61

```
taattttcca ttggcgataa gtttattaag ggtcttacc                              39
```

<210> SEQ ID NO 62
<211> LENGTH: 36
<212> TYPE: DNA
<213> ORGANISM: Artificial
<220> FEATURE:
<223> OTHER INFORMATION: synthetic primer

<400> SEQUENCE: 62

```
aacaatttca acaagaaca acaaaatgct ttctat                                  36
```

<210> SEQ ID NO 63
<211> LENGTH: 36
<212> TYPE: DNA
<213> ORGANISM: Artificial
<220> FEATURE:
<223> OTHER INFORMATION: synthetic primer

<400> SEQUENCE: 63

```
tttttgttg tcttcctctt ttggtgcttg agcatc                                  36
```

<210> SEQ ID NO 64
<211> LENGTH: 36
<212> TYPE: DNA
<213> ORGANISM: Artificial
<220> FEATURE:
<223> OTHER INFORMATION: synthetic primer

<400> SEQUENCE: 64

```
aacaatttca acaagaaca acaaaatgct ttctat                                  36
```

<210> SEQ ID NO 65
<211> LENGTH: 30
<212> TYPE: DNA
<213> ORGANISM: Artificial
<220> FEATURE:
<223> OTHER INFORMATION: synthetic primer

<400> SEQUENCE: 65

```
gttaggtaaa tgtaaagttt catagaaagc                                        30
```

<210> SEQ ID NO 66
<211> LENGTH: 30
<212> TYPE: DNA
<213> ORGANISM: Artificial
<220> FEATURE:
<223> OTHER INFORMATION: synthetic primer

<400> SEQUENCE: 66

```
taactgaaga acaacgtaac ggcttcatcc                                        30
```

<210> SEQ ID NO 67
<211> LENGTH: 30
<212> TYPE: DNA
<213> ORGANISM: Artificial
<220> FEATURE:
<223> OTHER INFORMATION: synthetic primer

<400> SEQUENCE: 67

```
tgatggatcg tctttagggc tttggatgaa                                        30
```

<210> SEQ ID NO 68
<211> LENGTH: 30
<212> TYPE: DNA
<213> ORGANISM: Artificial
<220> FEATURE:

<223> OTHER INFORMATION: synthetic primer

<400> SEQUENCE: 68
gtgagcaaag aaattttagc agaagctaaa                                         30

<210> SEQ ID NO 69
<211> LENGTH: 36
<212> TYPE: DNA
<213> ORGANISM: Artificial
<220> FEATURE:
<223> OTHER INFORMATION: synthetic primer

<400> SEQUENCE: 69 tttttgttg tcttcctctt ttggtgcttg agcatc                                  36

<210> SEQ ID NO 70
<211> LENGTH: 111
<212> TYPE: DNA
<213> ORGANISM: Artificial
<220> FEATURE:
<223> OTHER INFORMATION: synthetic primer

<400> SEQUENCE: 70
aagcttcaaa ctaataagaa aaggtgact gctcaagaat tagattacct aactgggagc        60
gggtttccga gtccttatta tagccctgct tttacaaaag gggaaaagct t               111

<210> SEQ ID NO 71
<211> LENGTH: 111
<212> TYPE: DNA
<213> ORGANISM: Artificial
<220> FEATURE:
<223> OTHER INFORMATION: synthetic primer

<400> SEQUENCE: 71
aagcttttcc cctttgtaa aagcagggct ataataagga ctcggaaacc cgctcccagt        60
taggtaatct aattcttgag cagtcacctt tttcttatta gtttgaagct t               111

<210> SEQ ID NO 72
<211> LENGTH: 36
<212> TYPE: DNA
<213> ORGANISM: Artificial
<220> FEATURE:
<223> OTHER INFORMATION: synthetic primer

<400> SEQUENCE: 72
aagcttaaat atgaacaagg tggcaatatt gtagat                                 36

<210> SEQ ID NO 73
<211> LENGTH: 36
<212> TYPE: DNA
<213> ORGANISM: Artificial
<220> FEATURE:
<223> OTHER INFORMATION: synthetic primer

<400> SEQUENCE: 73
aagctttgta tcttcaaagt caacactatt gtgtcc                                 36

<210> SEQ ID NO 74
<211> LENGTH: 58
<212> TYPE: PRT
<213> ORGANISM: Artificial
<220> FEATURE:
<223> OTHER INFORMATION: synthetic peptide

<400> SEQUENCE: 74

```
Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 75
<211> LENGTH: 58
<212> TYPE: PRT
<213> ORGANISM: Artificial
<220> FEATURE:
<223> OTHER INFORMATION: synthetic peptide

<400> SEQUENCE: 75

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 76
<211> LENGTH: 61
<212> TYPE: PRT
<213> ORGANISM: Artificial
<220> FEATURE:
<223> OTHER INFORMATION: synthetic peptide

<400> SEQUENCE: 76

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 77
<211> LENGTH: 57
<212> TYPE: PRT
<213> ORGANISM: Artificial
<220> FEATURE:
<223> OTHER INFORMATION: synthetic peptide

<400> SEQUENCE: 77

Met Ala Gln His Asp Glu Ala Gln Gln Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Asp Pro Ser Gln Ser Ala Asn Val Leu Gly Glu Ala Gln
        35                  40                  45

Lys Leu Asn Asp Ser Gln Ala Pro Lys
    50                  55

<210> SEQ ID NO 78
```

```
<211> LENGTH: 54
<212> TYPE: PRT
<213> ORGANISM: Artificial
<220> FEATURE:
<223> OTHER INFORMATION: synthetic peptide

<400> SEQUENCE: 78

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala
    50

<210> SEQ ID NO 79
<211> LENGTH: 58
<212> TYPE: PRT
<213> ORGANISM: Artificial
<220> FEATURE:
<223> OTHER INFORMATION: synthetic peptide

<400> SEQUENCE: 79

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```